(12) United States Patent
Carroll et al.

(10) Patent No.: US 9,864,837 B2
(45) Date of Patent: Jan. 9, 2018

(54) CLINICAL QUALITY ANALYTICS SYSTEM WITH RECURSIVE, TIME SENSITIVE EVENT-BASED PROTOCOL MATCHING

(71) Applicant: Accenture Global Services Limited, Dublin (IE)

(72) Inventors: Dennis Carroll, Leander, TX (US); Anh-Hoang Vo, Austin, TX (US); German Acuna, Austin, TX (US); Cecil O. Lynch, Granite Bay, CA (US); Erica Creen, Chicago, IL (US)

(73) Assignee: ACCENTURE GLOBAL SERVICES LIMITED, Dublin (IE)

( * ) Notice: Subject to any disclaimer, the term of this patent is extended or adjusted under 35 U.S.C. 154(b) by 200 days.

(21) Appl. No.: 13/781,397

(22) Filed: Feb. 28, 2013

(65) Prior Publication Data

US 2014/0244295 A1    Aug. 28, 2014

(51) Int. Cl.
*G06F 19/00* (2011.01)
*G06Q 10/06* (2012.01)

(52) U.S. Cl.
CPC .......... *G06F 19/322* (2013.01); *G06F 19/327* (2013.01); *G06F 19/3431* (2013.01); *G06F 19/3487* (2013.01); *G06Q 10/0633* (2013.01)

(58) Field of Classification Search
CPC .. G01N 2800/52; G06Q 50/24; G06F 19/322; G06F 19/3443; G06F 19/345; G06F 19/325; G06F 19/34; C12Q 2600/112
USPC .......................................................... 705/2–4
See application file for complete search history.

(56) References Cited

U.S. PATENT DOCUMENTS

| 6,539,339 | B1 | 3/2003 | Berry et al. |
| 8,108,781 | B2* | 1/2012 | Laansoo et al. ............... 715/751 |
| 2006/0123421 | A1 | 6/2006 | Loboz |
| 2008/0133275 | A1* | 6/2008 | Haug ..................... G06Q 10/06 705/3 |
| 2009/0024414 | A1* | 1/2009 | Mansour ............... G06F 19/322 705/3 |
| 2010/0226342 | A1 | 9/2010 | Collins et al. |
| 2010/0318549 | A1* | 12/2010 | Mayr .................... G06F 19/322 707/759 |
| 2011/0022413 | A1* | 1/2011 | Markessini ....................... 705/3 |

(Continued)

FOREIGN PATENT DOCUMENTS

| CN | 101315652 A | 12/2008 |
| WO | 2012092589 A1 | 7/2012 |
| WO | WO 2012/092589 | 7/2012 |

OTHER PUBLICATIONS

R.S. Mans et al: "Application of Process Mining in Healthcare—A Case Study in a Dutch Hospital", Networked Digital Technologies, Jan. 1, 2009, pp. 425-438, Berlin, Heidelberg.

(Continued)

*Primary Examiner* — Minnah Seoh
*Assistant Examiner* — Teresa Williams
(74) *Attorney, Agent, or Firm* — Mannava & Kang, P.C.

(57) ABSTRACT

A clinical quality analytics system may include a data storage to store electronic medical record (EMR) data. The system may map events from the EMR data to a process map through a recursive matching process. The mapping may include recursively matching the events to nodes in threads in a map based on event times and thread times. One of the recursions may be selected as a best fit based on metrics determined for the recursions.

16 Claims, 21 Drawing Sheets

(56) References Cited

U.S. PATENT DOCUMENTS

| | | | |
|---|---|---|---|
| 2011/0196704 A1* | 8/2011 | Mansour | G06F 17/30507 705/3 |
| 2013/0253839 A1* | 9/2013 | Friedlander et al. | 702/19 |
| 2013/0253892 A1* | 9/2013 | Friedlander et al. | 703/11 |
| 2013/0275149 A1* | 10/2013 | Gaines | G06F 19/325 705/3 |

OTHER PUBLICATIONS

A Lvaro Rebuge et al: "Business process analysis in healthcare environments: A methodology based on process mining", Information Systems, vol. 37, No. 2, Apr. 2012.
Dijkman R et al: "Similarity of Business process models: Metrics and evaluation", Information Systems, Pergamon Press, Exford, GB, vol. 36, No. 2, Apr. 1, 2011, pp. 498-516.
Remco Dijkman et al: "Graph Matching Algorithms for Business Process Model Similarity Search", Sep. 8, 2009, Business Process Management, Springer Berlin, Heidelberg, Berlin, Heidelberg, pp. 48-63.
"Extended European Search Report" on European Patent Application No. 14000704.8, dated Jul. 14, 2014, European Patent Office.
"Patent Examination Report No. 1" on Australia Patent Application No. 2014200966, dated Apr. 23, 2014, IP Australia, 3 pages.
Wang Jia, "Research on Conformance Checking method based on Process Mining", Hunan, P.R. China, Dec. 15, 2011, 81 pages.
English language translation of Second Office Action, "Chinese Patent Application No. 2014100758508", The Patent Office of P.R. China, dated Apr. 19, 2017, 4 pages.

* cited by examiner

HOME  MY PROJECTS  CREATE NEW PROJECT  DATA MANAGEMENT  ADMIN  SEARCH

MESSAGES & ALERTS ▼  PROJECT SETTINGS ▼  RELATED PROJECTS ▼

SEPSIS

500

| | MEASURES AND OUTCOMES | | | | |
|---|---|---|---|---|---|
| OVERVIEW | [NEW] [COPY] [TEST] [DELETE] | | | | |
| PLANNING | # | NAME | PROTOCOL | TYPE | CALCULATION NOTES LAST MODIFIED |
| PROTOCOLS | 1 | ☐ RESOLVED SEPSIS CASES | SEPSIS_COMPREHENSIVE | OUTCOME COUNT | 📄 01/02 |
| MINING | 2 | ☐ SEPSIS MORTALITY CASES | SEPSIS_COMPREHENSIVE | OUTCOME COUNT | 📄 01/06 |
| MEASURES AND OUTCOMES ▼ | 3 | ☐ PROGRESSION FROM SEPSIS TO ADVANCED SEPSIS | SEPSIS_COMPREHENSIVE | OUTCOME COUNT | 📄 01/25 |
| POPULATIONS | 4 | ☐ RESOLVED SEVERE SEPSIS CASES | SEPSIS_COMPREHENSIVE | OUTCOME COUNT | 📄 01/08 |
| SCORING | 5 | ☐ SEVERE SEPSIS MORTALITY CASES | SEPSIS_COMPREHENSIVE | OUTCOME COUNT | 📄 01/08 |
| REPORTS | 6 | ☐ PROGRESSION FROM SEVERE SEPSIS TO SEPTIC SHOCK | SEPSIS_COMPREHENSIVE | OUTCOME COUNT | 📄 01/10 |
| CLINICAL REVIEW | 7 | ☐ RESOLVED SEPTIC SHOCK CASES | SEPSIS_COMPREHENSIVE | OUTCOME COUNT | 📄 01/18 |
| PROJECT SCORECARD | 8 | ☐ SEPTIC SHOCK MORTALITY CASES | SEPSIS_COMPREHENSIVE | OUTCOME COUNT | ADD 01/14 |
| DOCUMENTS | 9 | ☐ SEPSIS PROGRESSION RATE % | SEPSIS_COMPREHENSIVE | MEASURE PERCENT | 📄 01/27 |
| WIKI | 10 | ☐ SEVERE SEPSIS PROGRESSION RATE % | SEPSIS_COMPREHENSIVE | MEASURE PERCENT | 📄 01/26 |
| | 11 | ☐ SEPSIS PROGRESSION COMPLIANCE % | SEPSIS_COMPREHENSIVE | MEASURE PERCENT | 📄 01/15 |
| | 12 | ☐ SEVERE SEPSIS PROGRESSION COMPLIANCE RATE % | SEPSIS_COMPREHENSIVE | MEASURE PERCENT | 📄 01/09 |
| | 13 | ☐ OVERALL COMPLIANCE % | SEPSIS_COMPREHENSIVE | MEASURE PERCENT | ADD 01/09 |
| | 14 | ☐ SEPSIS COMPLIANCE % | SEPSIS_COMPREHENSIVE | MEASURE PERCENT | 📄 01/09 |
| | 15 | ☐ SEVERE SEPSIS COMPLIANCE % | SEPSIS_COMPREHENSIVE | MEASURE PERCENT | 📄 01/10 |
| | 16 | ☐ SEPTIC SHOCK COMPLIANCE % | SEPSIS_COMPREHENSIVE | MEASURE PERCENT | 📄 01/13 |
| | 17 | ☐ MORTALITY COMPLIANCE % | SEPSIS_COMPREHENSIVE | MEASURE PERCENT | 📄 01/12 |
| | 18 | ☐ RESOLVED COMPLIANCE % | SEPSIS_COMPREHENSIVE | MEASURE PERCENT | ADD 01/21 |
| | 19 | ☐ COMPLIANCE RATE FOR MD ABX ORDER W/IN 1 HR % | SEPSIS_COMPREHENSIVE | MEASURE PERCENT | 📄 01/04 |
| | [NEW] [COPY] [TEST] [DELETE] | | | | |

SEPSIS

| | |
|---|---|
| OVERVIEW | |
| PLANNING | |
| PROTOCOLS | |
| MINING | |
| MEASURES AND OUTCOMES | |
| POPULATIONS ▲ | |
| SCORING | |
| REPORTS | |
| CLINICAL REVIEW | |
| PROJECT SCORECARD | |
| DOCUMENTS | |
| WIKI | |

MESSAGES & ALERTS ▼   PROJECT SETTINGS ▼   RELATED PROJECTS ▼

700

SEPSIS POPULATIONS ▶ EDIT SEPSIS_ALL

NAME: SEPSIS_ALL
DESCRIPTION: FULL SEPSIS POPULATION
NOTES: IF THE PATIENT HAS CONFIRMED OR SUSPECTED NEW INFECTION INDICATED BY ONE OF THE FOLLOWING SIGNS OR SYMPTOMS: NEW PAIN

| | ATTRIBUTE | RELATIONSHIP | VALUES |
|---|---|---|---|
| ☐ | VITALS: NEW PAIN | EQUAL TO | YES |
| | | OR | |
| ☐ | LDA: DRAINAGE ISSUES | EQUAL TO | YES |
| | | OR | |
| ☐ | REVIEW OF SYSTEMS: RESPIRATORY DISTRESS | EQUAL TO | YES |
| | | OR | |
| ☐ | LAB RESULTS: URINE ANALYSIS MACROSCOPIC: URINE CLARITY | EQUAL TO | HAZY |
| ☐ | | AND | |
| ☐ | | 2 OF THE FOLLOWING | |
| ☐ | VITALS: TEMPERATURE | GREATER THAN | 38° C |
| | | OR | |
| ☐ | VITALS: TEMPERATURE | LESS THAN | 36° C |
| ☐ | VITALS: PULSE | GREATER THAN | 90 |
| ☐ | VITALS: RESPIRATORY RATE | GREATER THAN | 20 BEATS/MIN |
| | | OR | |
| ☐ | LAB RESULTS: PCO2 (A), ISTAT | LESS THAN | 32 mm/Hg |
| ☐ | LAB RESULTS: AUTOMATED BLOOD COUNT - WBC | LESS THAN | 4 |
| | | OR | |
| ☐ | LAB RESULTS: BAND NEUTROPHILS | GREATER THAN | 10% |
| ⊕ | | | |

[SAVE] [COPY] [GROUP] [UNGROUP] [RUN] [SCHEDULE] [TEST] [DELETE]

| HOME | MY PROJECTS | CREATE NEW PROJECT | DATA MANAGEMENT | ADMIN | SEARCH | | |
|---|---|---|---|---|---|---|---|

900

| SEPSIS | | MESSAGES & ALERTS ▼ | PROJECT SETTINGS ▼ | RELATED PROJECTS ▼ |
|---|---|---|---|---|

| OVERVIEW | SELECTION | SAVED RESULTS | VARIANCE ANALYSIS - OUTCOME | NODE COMPLIANCE - MD SUMMARY |
|---|---|---|---|---|
| PLANNING | REPORT PARAMETERS | | | EXPAND |
| PROTOCOLS | REPORT RESULT | | | COLLAPSE |
| MINING | VIEW: ☐ TABLE | | | |

| MEASURES AND OUTCOMES | NODE COMPLIANCE: MD SUMMARY | | | | | | | |
|---|---|---|---|---|---|---|---|---|
| POPULATIONS | ATTENDING PROVIDER | # OF CASES | # OF SEPSIS CASES | # OF SEVERE SEPSIS CASES | # OF SEPTIC SHOCK CASES | MORTAL-ITIES | RE-SOLVED | COMPLI-ANCE % | AVERAGE TOTAL CHARGES | AVE LOS |
| SCORING | DR. 0007 | 4 | 4 | 0 | 0 | 1 | 3 | 70.0% | $172,274 | 8.12 |
| REPORTS ▸ | DR. 0009 | 4 | 4 | 0 | 0 | 1 | 3 | 67.5% | $381,595 | 16.53 |
| CLINICAL REVIEW | DR. 0038 | 3 | 3 | 0 | 0 | 0 | 3 | 78.3% | $84,099 | 4.10 |
| | DR. 0047 | 3 | 0 | 3 | 0 | 1 | 3 | 76.7% | $219,259 | 10.75 |
| PROJECT SCORECARD | DR. 0026 | 3 | 3 | 0 | 0 | 0 | 2 | 66.7% | $56,852 | 2.46 |
| DOCUMENTS | DR. 0028 | 3 | 3 | 0 | 0 | 0 | 3 | 66.7% | $122,649 | 6.86 |
| WIKI | DR. 0035 | 3 | 0 | 0 | 0 | 0 | 3 | 66.7% | $122,338 | 5.52 |
| | DR. 0064 | 3 | 3 | 0 | 3 | 0 | 3 | 66.7% | $194,676 | 8.32 |
| | DR. 0083 | 3 | 3 | 0 | 0 | 0 | 3 | 65.0% | $243,200 | 9.80 |
| | DR. 0031 | 3 | 0 | 0 | 0 | 0 | 3 | 63.3% | $79,640 | 4.70 |
| | DR. 0011 | 3 | 3 | 0 | 0 | 0 | 3 | 60.0% | $239,602 | 9.60 |
| | DR. 0058 | 2 | 0 | 2 | 0 | 0 | 2 | 80.0% | $267,543 | 10.07 |
| | DR. 0043 | 2 | 0 | 2 | 0 | 0 | 2 | 77.5% | $132,722 | 7.78 |
| | DR. 0053 | 2 | 0 | 2 | 0 | 0 | 2 | 77.5% | $85,606 | 3.60 |
| | DR. 0057 | 2 | 0 | 2 | 0 | 0 | 2 | 77.5% | $89,439 | 4.94 |
| | DR. 0050 | 2 | 0 | 0 | 0 | 0 | 2 | 75.0% | $136,405 | 5.11 |
| | DR. 0005 | 2 | 2 | 0 | 0 | 0 | 2 | 70.0% | $114,194 | 5.57 |

COMPUTER | PROTECTED MODE: OFF

FIG. 9

```
Simulate_Protocol_Function()
{
  if it is not mathematically possible to improve matching
          return;
  otherwise
          select thread with earliest timestamp
          switch (thread's current node type)
                  START NODE:    Advance thread to node linked from start node ACTIVITY NODE or DECISION NODE:
                          update metrics for the node
                          loop through each remaining event attached to the node
                                  if the event is within the time criteria for the event
                                          Set thread time to selected event's time
                                          advance thread to next node
                                          Simulate_Protocol_Function ()
                          if this thread has not exceed the consecutive skip limit
                                  for each link from this node
                                          advance thread to next node
                                          Simulate_Protocol_Function ()
                  RENDEVOUS AND CONTINUE:
                          loop through each outgoing link from this node
                                  launch a new thread on the node the link leads to
                                  copy parent thread's timestamp to the new thread
                                  Simulate_Protocol_Function ()
                  STOP THIS THREAD:
                          mark this thread thread as halted
                          Simulate_Protocol_Function ()

STOP ALL THREADS EXCEPT THIS THREAD:
                          stop all other threads except for this one
                          loop through each outgoing link from this node
                                  launch a new thread on the node the link leads to
                                  copy parent thread's timestamp to the new thread
                                  Simulate_Protocol_Function ()

PROTOCOL STOP:
                          check to see if accumumlated pattern-matched path is the best and save it if it is
```

FIG. 17

CLINICAL QUALITY ANALYTICS SYSTEM WITH RECURSIVE, TIME SENSITIVE EVENT-BASED PROTOCOL MATCHING

BACKGROUND

In an organization providing medical care, records are often kept in the form of electronic medical records (EMRs). For example, a physician may enter notes into a computer to make them part of an EMR for a patient, or the notes are entered on a chart or are audio recorded and later transcribed and entered to become part of an EMR. The EMRs may be stored in a database and retrieved for reporting.

The reporting on the EMRs tends to be rudimentary. For example, EMRs may be viewed on a patient-by-patient basis, such as to view the existing data on the care previously provided to the patient. In some cases, reports may be generating on an aggregate level to view information on multiple patients. However, in many instances, this aggregate level of reporting is insufficient to understand the level of care being provided by an organization or to understand how to improve the quality of care. Part of the cause is that much of the data entered into the EMRs is text taken from caregiver's notes or dictations, which is difficult to quantify or report at an aggregate level.

In addition, in recent years, hospitals and other health care provider organizations have adopted evidence based clinical treatment guidelines called "medical protocols" as a part of their clinical quality programs. These guidelines are promulgated by a broad variety of health organizations, experts and industry authorities associated with specific medical specializations. These clinical treatment guidelines are utilized to diagnose and provide care for various illnesses, and in many instances hospitals and other caregivers utilize the guidelines to provide care. Many existing EMR systems are lacking in their ability to use EMRs to evaluate whether the guidelines are being followed or whether the guidelines are effective in improving care.

BRIEF DESCRIPTION OF THE DRAWINGS

Embodiments are described in detail in the following description with reference to the following figures. The embodiments are illustrated by way of example and are not limited in the accompanying figures in which like reference numerals indicate similar elements.

FIGS. 2-11 illustrate screenshots which may be generated by the CQA system, according to an embodiment;

FIG. 17 illustrates pseudocode for processing different types of nodes, according to an embodiment;

DETAILED DESCRIPTION OF THE EMBODIMENTS

For simplicity and illustrative purposes, the principles of the embodiments are described by referring mainly to examples thereof. In the following description, numerous specific details are set forth in order to provide a thorough understanding of the embodiments. It is apparent however, to one of ordinary skill in the art, that the embodiments may be practiced without limitation to these specific details. In some instances, well known methods and structures have not been described in detail so as not to unnecessarily obscure the description of the embodiments. Furthermore, different embodiments are described below. The embodiments may be used or performed together in different combinations.

According to an embodiment, a Clinical Quality Analytics (CQA) system renders a protocol, such as an industry clinical treatment guideline, into a process map. A process map may comprise a workflow that can be visualized on a display. The workflow comprises steps, which may be represented as nodes in the process map generated from the protocol. The workflow may comprise a time-based series of steps determined from the protocol to render care according to guidelines specified in the protocol. The time-based series of steps may be represented in chronological order of providing care from earliest to latest in the process map. The process map may comprise multiple threads and the threads may be executed in parallel and/or serially as is further described below. Metrics may be associated with the nodes, such as location and caregiver identity.

The CQA system is also operable to associate data from EMRs (e.g., events) with particular nodes in the process map, and based on the association, determine protocol compliance metrics. Reports may be generated to specify the compliance metrics and provide additional information related to measuring the quality of care and improving the quality of care.

Figure 1:
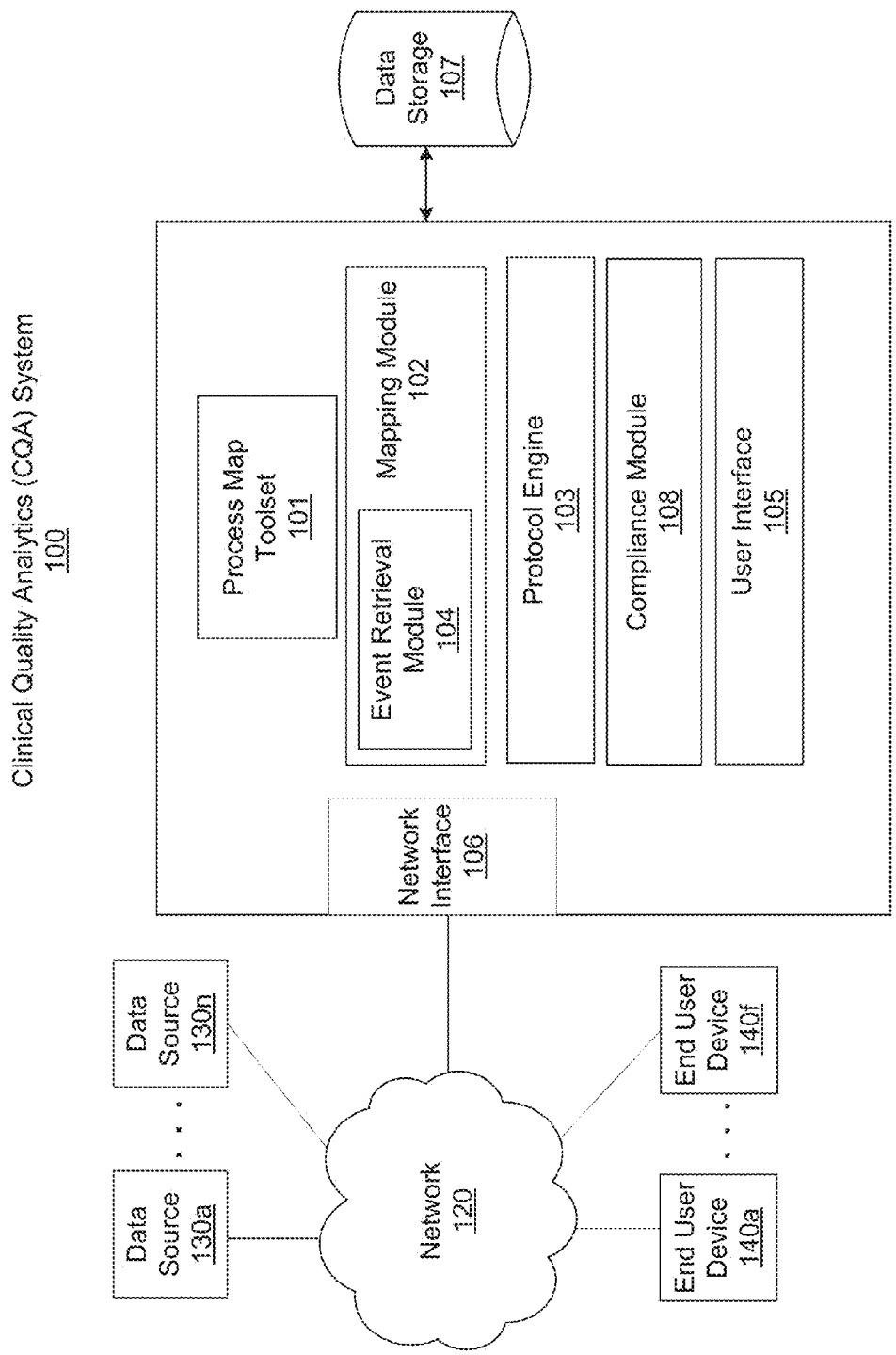
FIG. 1 illustrates a Clinical Quality Analytics (CQA) system, according to an embodiment.

FIG. 1 illustrates a CQA system 100, which may be connected to a network 120. Data Sources 130*a-n* are shown. The CQA system 100 may receive protocols, EMRs, and other information from the data sources 130*a-n*, for example, via the network 120. The data sources 130*a-n* may comprise electronic medical systems capturing medical data and generating EMRs from the medical data. The data sources 130*a-n* may comprise systems publishing protocols and other medical information. End user devices 140*a-f* are shown. The end user devices 140*a-f* may connect to the CQA system 100 to enter data and view compliance reporting and other information generated by CQA system 100. Although not shown, one or more of the data sources 130*a-n* and the end user devices 140*a-f* may be connected to the CQA system 100 through a direct link, rather than a network. For example, the CQA system 100 may be part of an electronic medical system that generates EMRs and includes the CQA system 100. Also, the CQA system 100 may include I/O devices, such as a display, keyboard, mouse, etc., that allows users to enter and view data.

The CQA system 100 includes a process map toolset 101, a mapping module 102, a protocol engine 103, an event retrieval module 104, a user interface 105, a network interface 106 and a compliance module 108. Also, a data storage 107 is connected to the CQA system 100 to store any information used by the CQA system 100, such as EMRs, protocols, process maps, reports, etc. The data storage 107 may include a database or other type of storage system. The network interface 106 connects the CQA system 100 to the network 120. The user interface 105 may include a graphical user interface (GUI), which may be viewed on a display connected to the CQA system 100 or viewed on the end user devices 140a-f via network 120, which may include the Internet. The components of the CQA system 100 may comprise computer hardware, software or a combination.

The process map toolset 101 generates process maps from protocols, which may be published by medical experts, health organizations or other entities. The protocols for example are medically related and may include treatment guidelines for various illnesses or medical conditions. The protocols are not limited to illnesses or negative medical conditions. For example, the protocols may include procedures for cosmetic surgery or other medically-related guidelines. The process map toolset 101 provides a workspace that presents a protocol for example received from a health organization, and provides tools for generating a process map from the protocol. The protocol may be provided as text in a document or may be documented directly in the process map toolset 101. Information from the protocol may be extracted to generate a protocol outline. A user may use tools provided by the process map toolset 101 to generate a process map from the protocol and protocol outline. The workspace provided by the process map toolset 101 may comprise an editor and other features described in further detail below.

The process map toolset 101 allows a user to create query objects for nodes in a process map or to select existing query objects for the nodes. A query object retrieves events from the data storage 107 that are relevant to a particular node. Query objects include predetermined concept identifiers (IDs) or a link or pointer to the predetermined concept IDs that include medical terms determined from medical standards or organizations publishing standard medical terms. The concept IDs may include categories. EMR data including events stored in the data storage 107 may also include the concept IDs. For example, a user creates a query object for a node in a gestational diabetes process map. The node may be related to observations. The process map toolset 101 provides a drop down menu presenting concept IDs that may be selected by the user for example via the user interface user 105. The user selects observations, and then selects diabetes, and then selects gestational diabetes. Then a query object is generated or selected from a pre-existing set of query objects and stored for the node including concept IDs for observations, diabetes, and gestational diabetes. For example, a pre-existing query object called "diabetes" is selected and populated with a selected parameter that states the type is "gestational" and then the new query object is stored with the node. In other examples, concept IDs may be used for orders, labs, results, procedures, and medication administration. In another example, the node may require an oximetry reading, and a concept ID from a medical standard such as the Systematized Nomenclature of Medicine (SNOMED) is selected for the reading, and another concept ID is selected for one of six ways to perform the reading. The query object may comprise a structured query language (SQL) statement including one or more of the concept IDs that can be called by the event retrieval module 104 to retrieve events from the data storage 107 for the node.

The event retrieval module 104 retrieves events from the data storage 107 for nodes in a process map. The event retrieval module 104 may be a sub-module of the mapping module 102. A module or sub-module may include machine readable instructions executed by hardware, such as a processor. The retrieved events may be for a specific patient or a group of patients. A query objects may be created for each decision or activity node in the process map to retrieve events relevant to each node. The event retrieval module 104 may call the query objects to retrieve the relevant events. An event includes information for any action performed to provide care to a patient, such as lab results, vitals (e.g., measurements of patient vital functions which may be performed by a nurse or machine), orders for tests or medications, delivery of medications, medications administered to patient, physician notes, semi-static patient data (e.g., gender, age, weight, allergies, etc.), etc. The stored EMR data includes the events. The events may include a description of the action and attributes for the event, such as event time, location, caregiver, etc.

The mapping module 102 maps the retrieved events to the process map. The mapping may include identifying the events retrieved by the event retrieval module 104 for a node and assigning the events to the node. Assigning may include providing an indication for the stored event that associates the event with the node. The mapping module 102 may determine an event time for each event and order the events for a node or thread chronologically from earliest to latest. An event time may be an attribute stored in EMR data for an event. The event time may indicate when the event was performed, such as date and/or time.

The protocol engine 103 determines a best fit of the events mapped to the nodes in a process map. Multiple events may be mapped to decision or activity node in a process map. Also, multiple events may be examined together to assign events to nodes in the process map. The protocol engine 103 determines a sequence of the events mapped to the nodes that is a best fit for the protocol represented by the process map. For example, a process map may have multiple threads of nodes that may run concurrently. Compliance with a protocol may be measured by whether particular events were performed in a sequence represented by the threads in the process map. Given the events mapped to each of the nodes in the process map, the protocol engine 103 determines a sequence of the events for the nodes that is a best fit for the threads in the process map such that no event is included in the best fit if it occurred after one of the threads reached a termination point for the protocol. For example, blood pressure readings that occurred after a patient was admitted to the hospital may not apply to an emergency room protocol since an event called "admit patient" may have represented the end of the emergency room protocol. The best fitting sequence may be determined based on the event time for each event and a thread time for each thread. A recursive matching process may be performed to determine the best fit. The protocol engine 103 when performing the recursive matching may assign a missing event to a node. A missing event is an event that should have been performed at a given time but is being considered as not to have been performed. Also, through the recursive matching process, many possible sequences of events that match the threads in a process map may be determined. Metrics may be determined to identify the sequence of events that are a best fit. In one example, the metric comprises a ratio of matching events over the number of nodes traversed during the matching process. In this example, the optimal value for this metric is 1 and the numerator cannot exceed the denominator. This ratio may be used for a "look-ahead" to determine whether to abandon a sequence in the recursion as a best fit. For example, if the current numerator/denominator plus the remaining unmapped events added to both the numerator and denominator is less than the numerator/denominator ratio of the best fit to date then the sequence may be abandoned.

The compliance module 108 measures compliance with the protocol based on the best fitting sequence identified by the protocol engine 103. The compliance module 108 may generate reports via the user interface 105 indicating the level of compliance with the protocol. The level of compliance may be measured based on the number of missing events. The reports may identify when the quality of care falls short and may be used to detect metrics associated with the causes, such as where, when, how and by whom.

FIGS. 2-11 show examples of screenshots generated by the CQA system 100, for example, via the user interface 105 that illustrates various functions of the CQA system 100.

Figure 2:
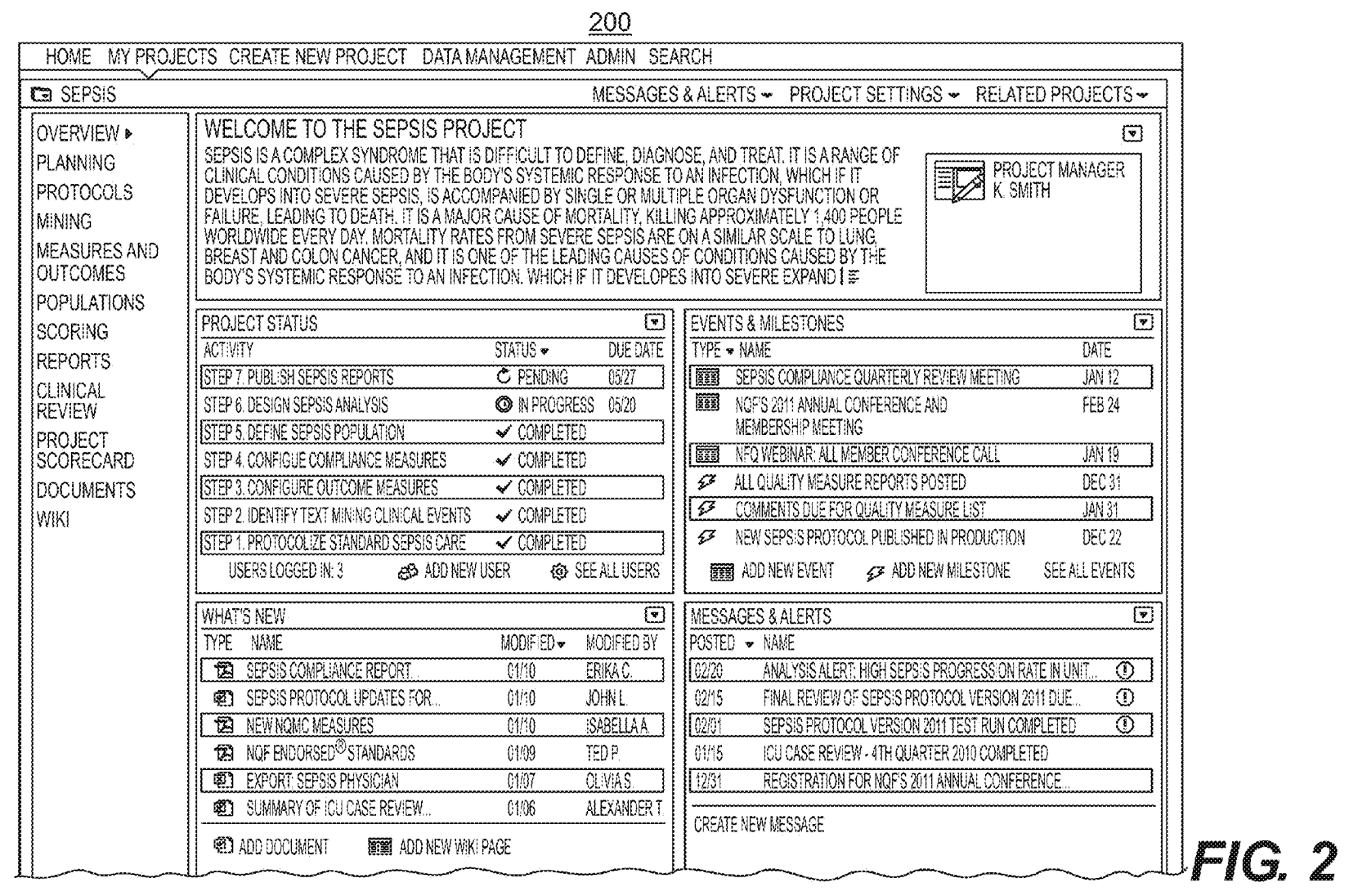

In one example, the CQA system 100 can be used to map a protocol for sepsis. Sepsis is a complex medical syndrome that is difficult to define, diagnose and treat. FIG. 2 shows a screenshot 200 of an overview for a sepsis project that may be created in the CQA system 100 to monitor compliance of quality of care provided to patients for a sepsis protocol. The screenshot 200 includes a project status that illustrates the steps performed with the CQA system 100 and their completion status. The steps include standardizing a protocol for sepsis to create a process map from the protocol; text mining clinical events in EMR data; configuring outcome and compliance measures for evaluating compliance with the protocol and overall quality of care; and defining a population of patients and sepsis analysis from the measures to generate reports. Other sections of the screenshot 200 show events and milestones for the project, messages and alerts and new documents added to the project. The events and milestones show the publication of a sepsis protocol which may be received and stored in the data storage 107 and may be used to create a process map for the sepsis protocol.

Figure 3:
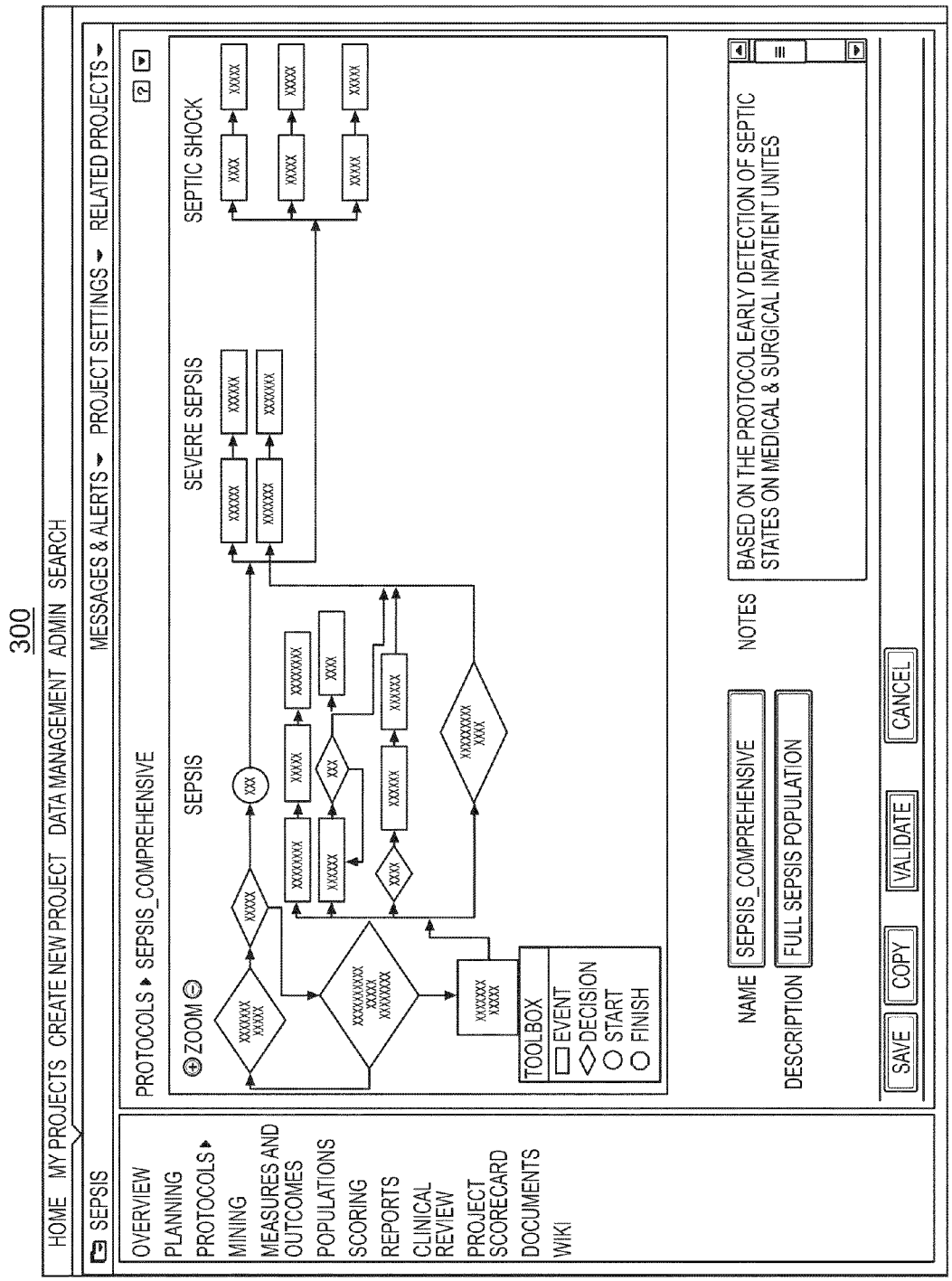

FIG. 3 shows a screenshot 300 of creating a process map from the sepsis protocol. The process map is labeled Sepsis_Comprehensive and is generally divided into three sections comprising Sepsis, Severe Sepsis and Septic Shock. In each section is the workflow that is created from the protocol. The workflow includes nodes, which may represent decision steps, such as shown as diamonds, or other event types of steps, shown as rectangles, circles or other shapes. The process map is a time-based series of nodes representing the workflow for providing care for patients that may have sepsis. The nodes may represent steps for diagnosing, measuring vitals, ordering tests, lab results, or any steps that may be used in providing of care for a sepsis patient. Time-based means the steps and nodes are followed in the sequence as shown to provide care. The process map may include more than one path that can be followed at the same time, so some steps may be performed simultaneously or substantially in parallel. The different paths are referred to as threads.

The process map toolset 101 provides a workspace for creating the process map based on the sepsis protocol. The workspace may include an editor as shown in FIG. 3. For example, a user can add, remove or modify nodes in the process map through the editor. Then, the process map can be validated, saved and copied as needed. The process map toolset 101 may generate an initial process map from the protocol. For example, text mining may be used to identify a series of steps from a published protocol and an initial process map is generated from the identified steps. The initial process map is shown in the editor, and a user may modify the process map as needed.

Each node in the process map may have attributes similar to the EMR data. Some of the attributes may include event type, time, location and caregiver. For example, one of the nodes in the process map is for the physician to order a lactic acid test every four hours. The attributes may include an event type, such as physician order. A location may include the department in which the physician works. The time may indicate when in the process map the physician is to perform the event of ordering this test. Other attributes may include event subtype, such as laboratory, and order frequency, such as every four hours. Result component, such as lactic acid, is another attribute that may be used for the laboratory event subtype. Attributes for steps may be entered by a user and may be displayed by clicking on a step in the process map.

The user may also create query objects for the nodes through the process map toolset 101. The process map toolset 101 may provide drop down menus for the user to select concept IDs for the query objects. The query objects may be stored with the process map in the data storage 107.

After the process map is generated and stored, the event retrieval module 104 retrieves events from the EMR data stored in the data storage 107 for the nodes in the process map, and the mapping module 102 maps the events to the nodes in the process map. For example, EMR data may be collected over a period time and periodically updated. The EMRs may be from a single entity, such as from a single hospital or physician's office, or may be from multiple entities. The EMR data may include some structured data, such as the identity of the caregiver and an event time of performing a medical event, and the EMR data may include unstructured data, such as text entered by a physician or nurse describing the care given to the patient.

The mapping module 102 temporally aligns events retrieved for each node. Temporally aligning events may include sorting the events assigned to each node by event time. The protocol engine 103 matches the temporally aligned events to the threads in the process map to determine a best fitting sequence of nodes as described in further detail below.

Figure 4:
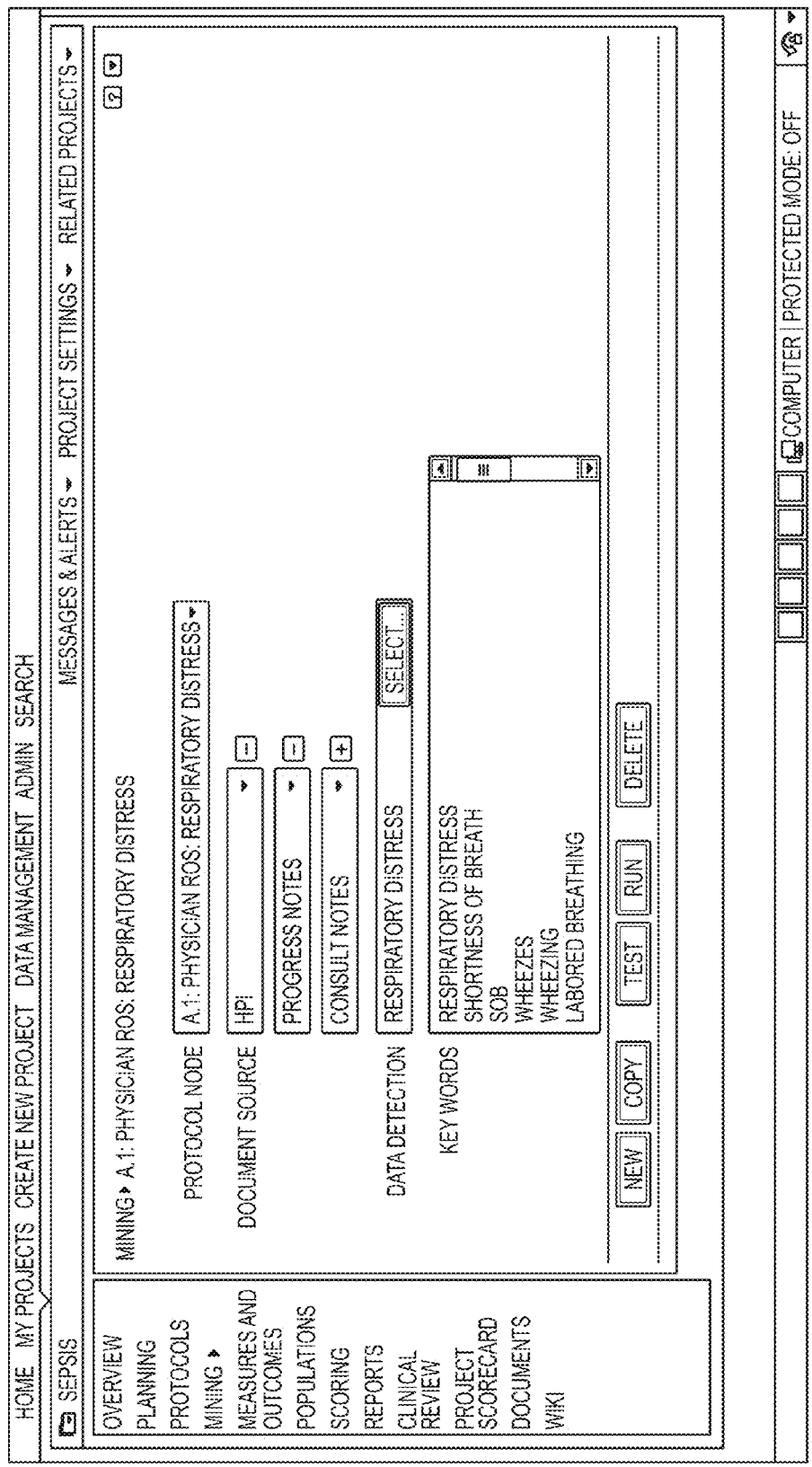

Data mining may be performed to extract attributes of the EMR data from the textual information in the EMR data. The text may include notes or other information entered by a caregiver, for example, in an unstructured format. FIG. 4 shows a screenshot 400 for entering data elements that may be used for text mining in order to extract data from a particular event in the process map. As shown in FIG. 4, the event from the process map is selected. Event is shown as "Protocol Node". In this example, the selected event is "A.1 Physician ROS: Respiratory Distress". This event A.1 may be a step in the process map for determining whether a patient has respiratory distress. The determination may be performed along with other steps to determine whether a patient qualifies a subsequent assessment.

Determination of respiratory distress may not be specified in structured data of EMRs. Instead, it may be specified in the text in notes in the EMRs or in other information. In the screenshot 400, the document source is selected, which may include EMR data or other information. HPI is selected which stands for history of present illness. Other documents that are selected are physician progress notes and consult notes. These documents are searched to identify whether the patients had respiratory distress.

The compliance module 108 may define analytic views that can be generated by the CQA system 100, and may determine key performance indicators (KPI's) and other metrics that are available to analyze the quality of care associated with the protocol. FIG. 5 shows an example of compliance metrics that be selected for analyzing the quality care provided around the sepsis protocol. The metrics identify the protocol or process map that is relevant, the type of metric (e.g., measurement or outcome), the calculation for determining the metric, notes and modification date.

Figure 6:
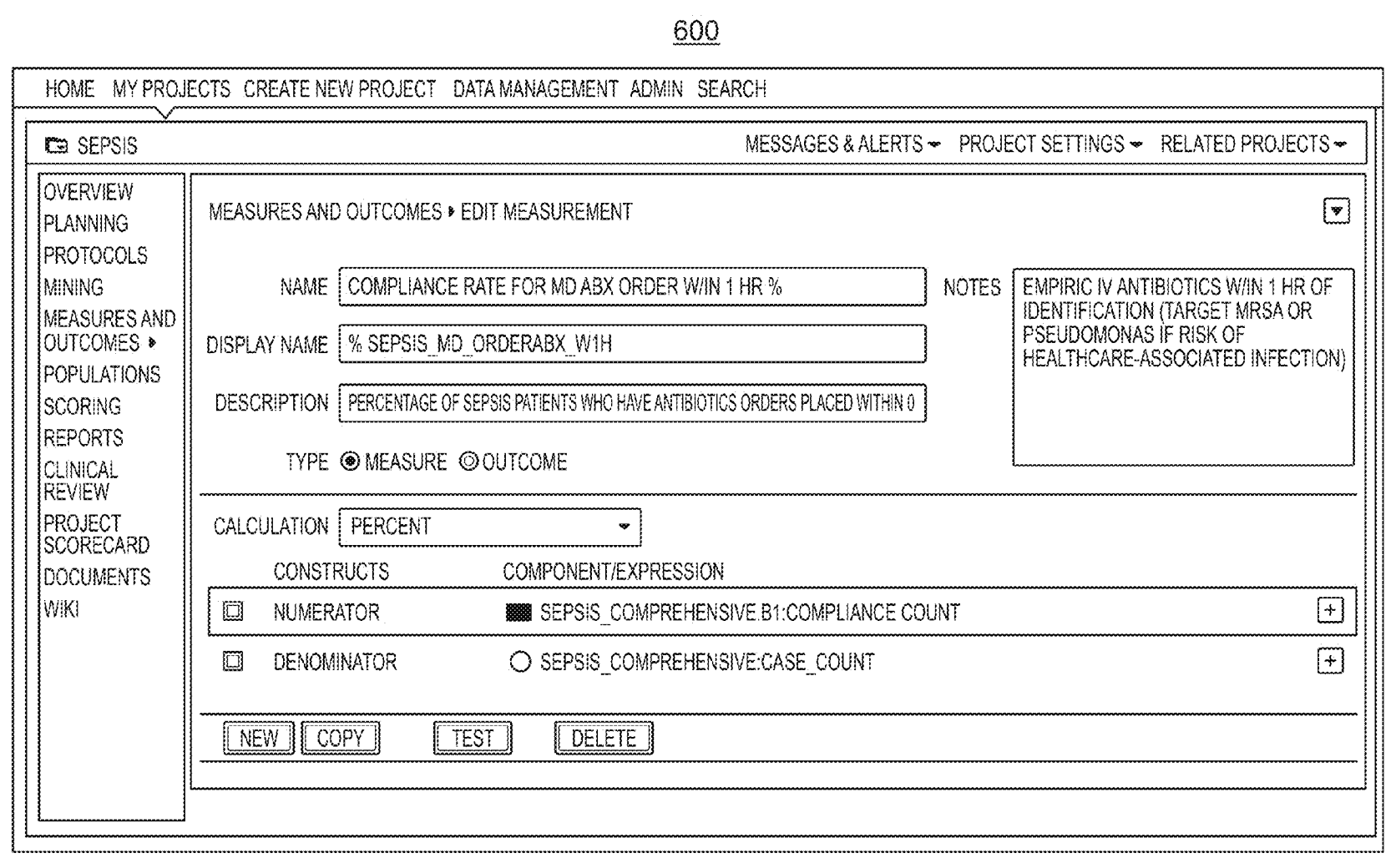

FIG. 6 shows a screenshot 600 for defining a metric. In this example, the metric is a compliance rate for an antibiotic order within the first hour. The metric is defined by specifying a name, display name and description, and specifying how the metric is calculated. In this example, the metric is defined as a percentage. The numerator is defined as the number of cases that comply with event node B1, which is the antibiotic order, and the denominator is defined as the number of cases that entered the comprehensive sepsis protocol.

In addition to determining metrics, KPIs and analytic views, the CQA system 100 may determine a population or the set of cases to be evaluated. FIG. 7 shows a screenshot 700 for selecting filters to identify the population of cases. The EMR data may include EMRs for millions of patients that were provided care for a variety of illnesses. In this example, filters are set to identify EMRs for patients that are suspected of having sepsis. The filters may include attributes and a value for each value and the relationship between the attribute and value. For example, filters may be selected in the screenshot 700 to identify all the cases where the patients have a vital sign of new pain=yes; a drainage issue=yes; respiratory distress=yes; lab results for urine analysis=hazy and any two of the filters shown in the bottom half of the screenshot 700. The filters may be combined through logic (e.g., AND, OR) to select the population. Also, a set of filters may be predetermined, such as shown in the screenshot 700, and some of the filters from the set are selected to identify the population. In many instances, EMR data gathered from the data mining process described above is compared to the filters to determine whether cases from the EMR data should be part of the population to be evaluated for compliance with the protocol. The EMR data is filtered by the selected filters to determine the population. Filtering may include determining EMR data that complies with filter conditions.

The population of cases may be evaluated based on the compliance metrics to determine compliance with the protocol and scores and reports may be generated to indicate compliance and variances from compliance and to provide analytical views to identify problems with particular individual caregivers, particular departments, particular shifts (e.g., day shift versus night shift), etc. A protocol may be evaluated against a whole population of patient encounters for a particular provider organization, such as a hospital. Reporting and drill-downs can be for the whole population in the whole protocol, for an individual patient encounter, for the whole population on a single node and/or for an individual encounter on a single node.

The analytic views generated by the CQA system 100 allow for the drill downs which may be used to identify the cause of problems. For example, an initial view may comprise a color-coded display of the process map. A node in the process map may be shown in red or yellow to indicate a high-level or medium-level of variance from the protocol. A user may click on a red node to drill down to additional information, such as compliance metrics for the department responsible for the event. Another drill down may include the metrics for the shifts for the department. Once a problematic shift is identified, another drill down may include compliance metrics for individuals in the shift. Then, remedies may be determined, such as additional training for individuals not adhering to the protocol. In another example, the metrics may identify that the protocol is not being followed during a shift change, so new internal shift change procedures for the department may be specified as a remedy.

The reports generated by the CQA system 100 may identify correlations between missing events and outcomes. An outcome may be a result of a medical condition or illness or a procedure and outcomes may vary. For example, outcomes for a particular type of cancer may be 1, 5 and 10 year survival rates. A report may identify that a missing event for treatment guidelines for a population of the cancer patients caused their survival rate to decrease from 10 years to 5 years or had no impact on their survival rate. This correlation is a statistical correlation between the missing event and a particular outcome that is impacted by the missing event. Reports showing the correlations can be generated by the CQA system 100.

Figure 8:
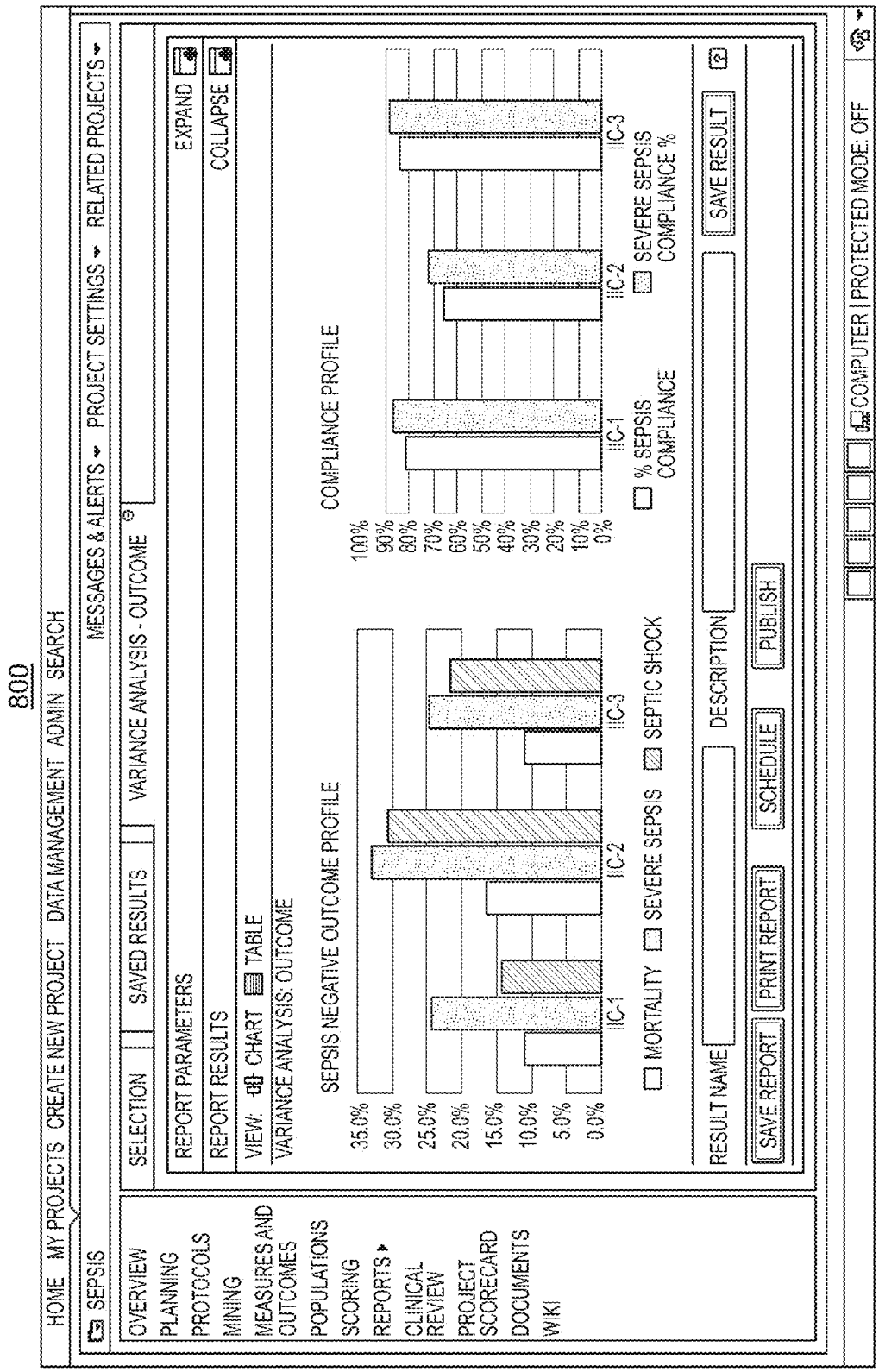

FIGS. 8-11 show examples of screenshots of reports generated by CQA system 100 based on comparisons performed by the CQA analytics engine 103. The reports may be based on the metrics defined and selected for the protocol. FIG. 8 shows a screenshot 800 of an example of an overall compliance report for the sepsis protocol. The screenshot 800 shows an outcome profile and a compliance profile. The profiles indicate the percentage of compliance for categories of the population.

Figure 10:
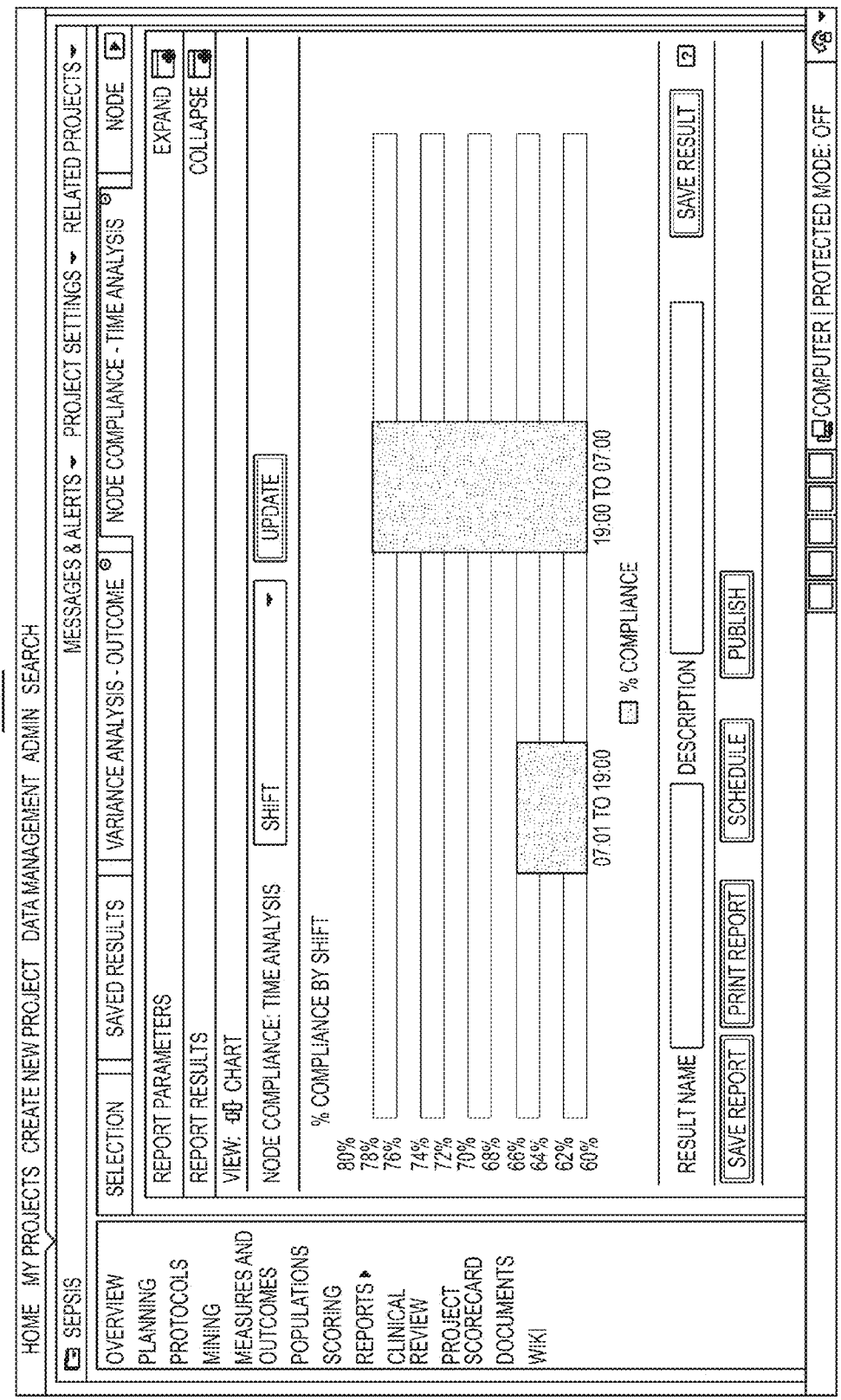
Figure 11:
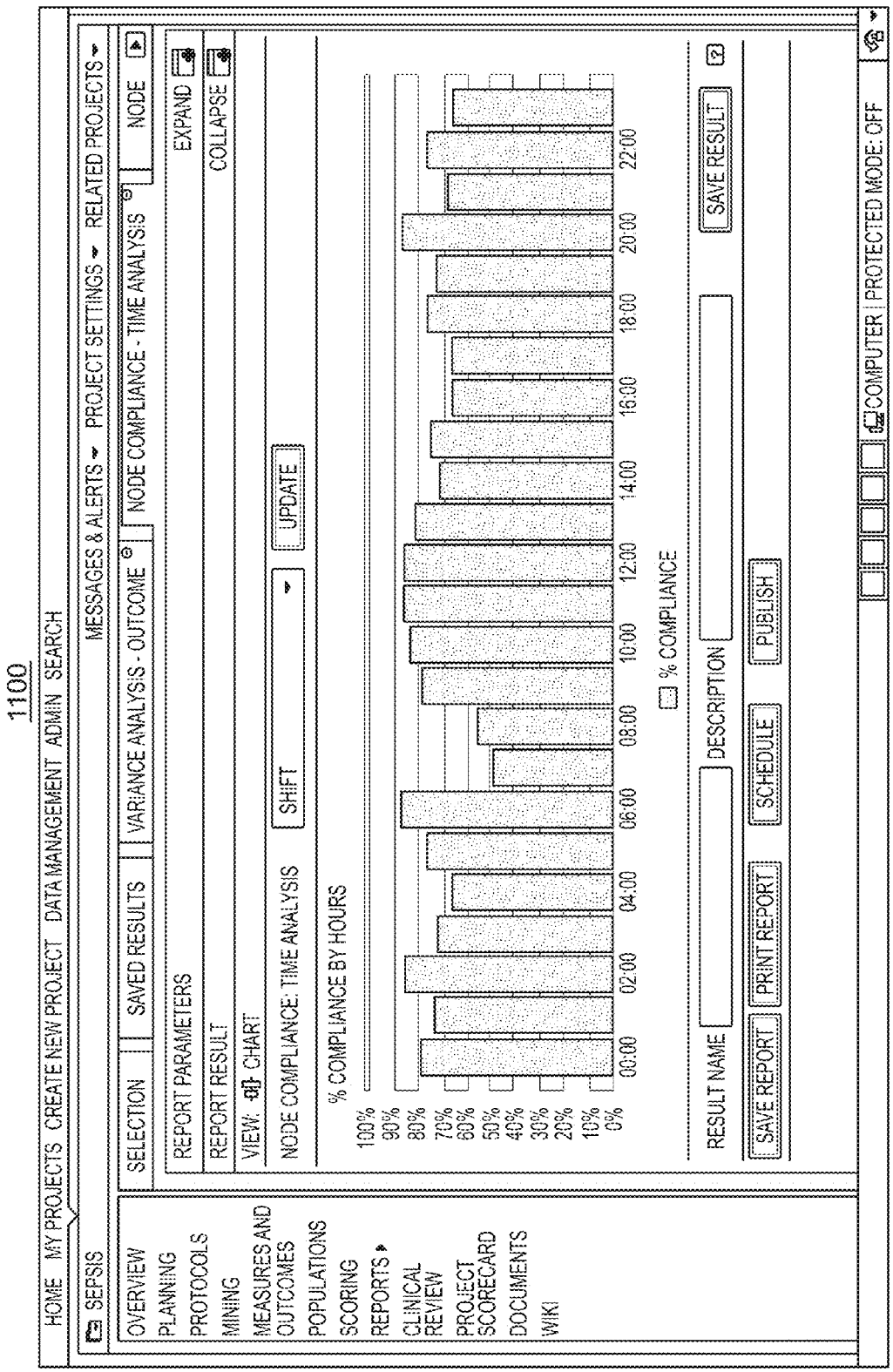

FIG. 9 shows a screenshot 900 of physician compliance. The report indicates the metrics for each physician including percentage of compliance and average total cost. This report may be used to identify physicians that are not complying or that are over-priced. FIGS. 10 and 11 show screenshots 1000 and 1100 providing reports of compliance percentages by shift. These reports may be used to evaluate compliance metrics on an hourly basis. The reports in the screenshots 900-1100 may be used as part of a drill down process to identify root causes of poor quality of care as it relates to the protocol.

As discussed above, the protocol engine 103 determines a sequence of the events mapped to the nodes that is a best fit for the protocol represented by the process map. Then, compliance with the protocol may be measured by determining whether events were performed for the nodes as required by the protocol and whether the events were performed in the proper sequence or workflow as required by the protocol. For example, a process map may have multiple threads of nodes that run concurrently. Given the events mapped to each of the nodes in the process map, the protocol engine 103 determines a sequence of the events for the nodes that is a best fit for the concurrent threads in the process map. A recursive matching process may be performed to determine the best fit.

Figure 12A:
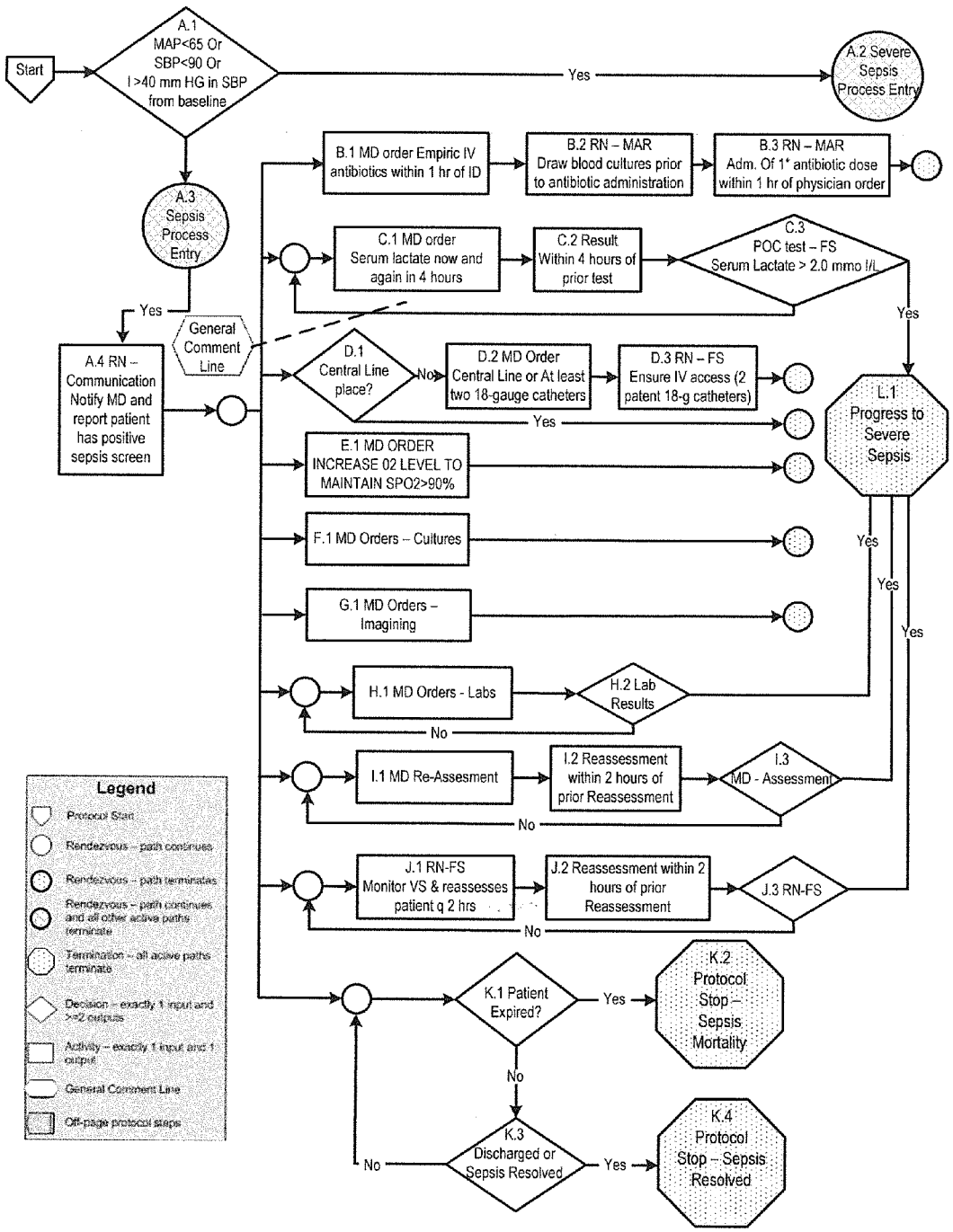
FIGS. 12A-B illustrate a process map and its threads, according to an embodiment.
Figure 12B:
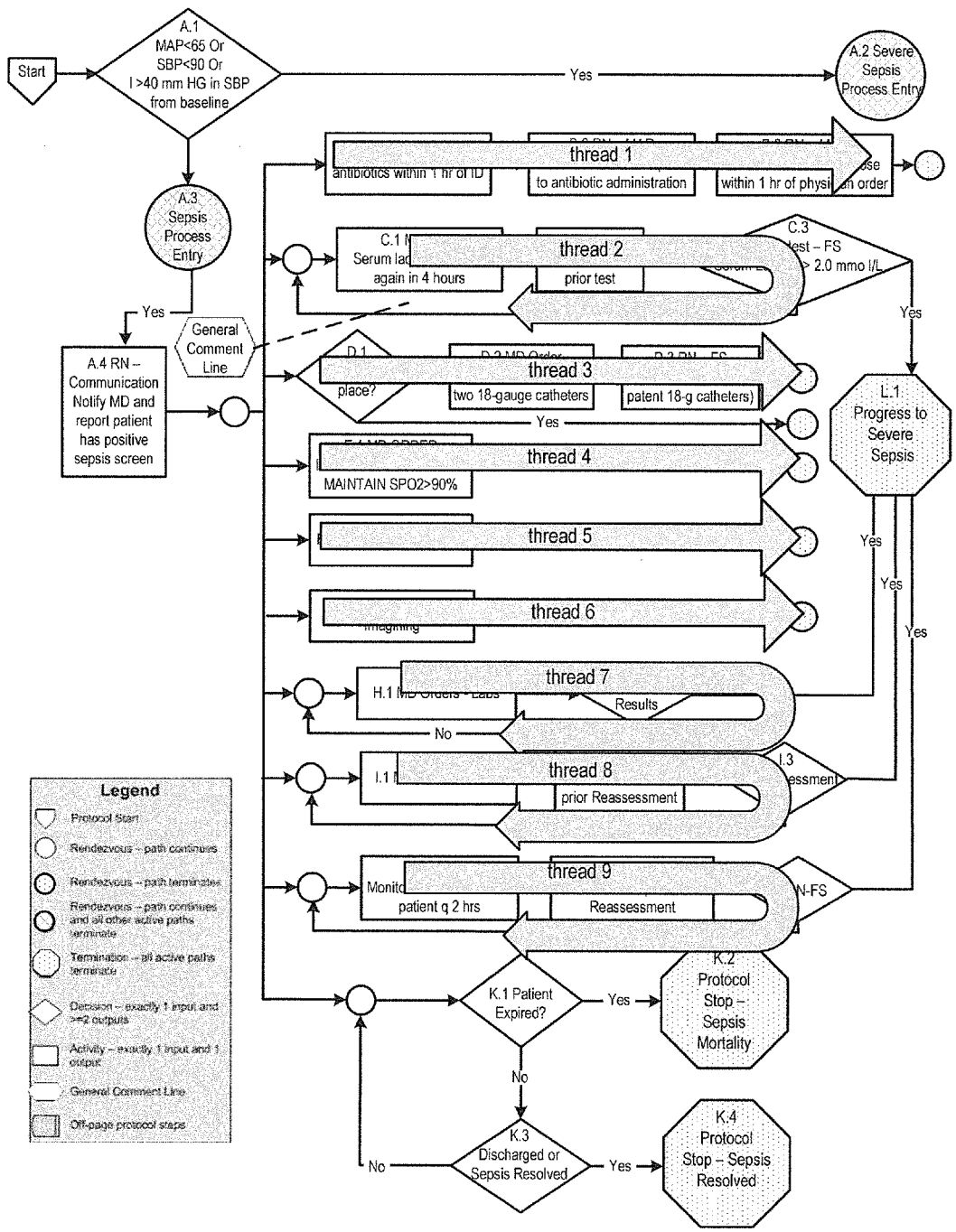

FIG. 12A shows a process map for a sepsis protocol that may be generated by the process map toolset 101 and stored in the data storage 107. The process map includes parallel flows, shown as threads 1-9 in FIG. 12B. A thread is a sequence of nodes that may be connected to another thread through a rendezvous point or that may terminate on a specific node. The process map includes parallel threads, and the threads may fork and rendezvous at certain nodes and depending on the events for a node, different threads may be followed to comply with the sepsis protocol.

Different types of nodes may be used in the process map to represent different actions and expected events for the protocol. Some examples of the types of nodes include: a start node identifying a start of the protocol; an activity or decision node wherein at least one event is to take place for the activity or decision node; a rendezvous and continue node wherein a new thread is launched from the rendezvous and continue node; a stop thread node (e.g., rendezvous path terminates); a stop all threads except current thread node;

and a protocol stop node identifying an end of the protocol (e.g., all active threads terminate).

Figure 13:
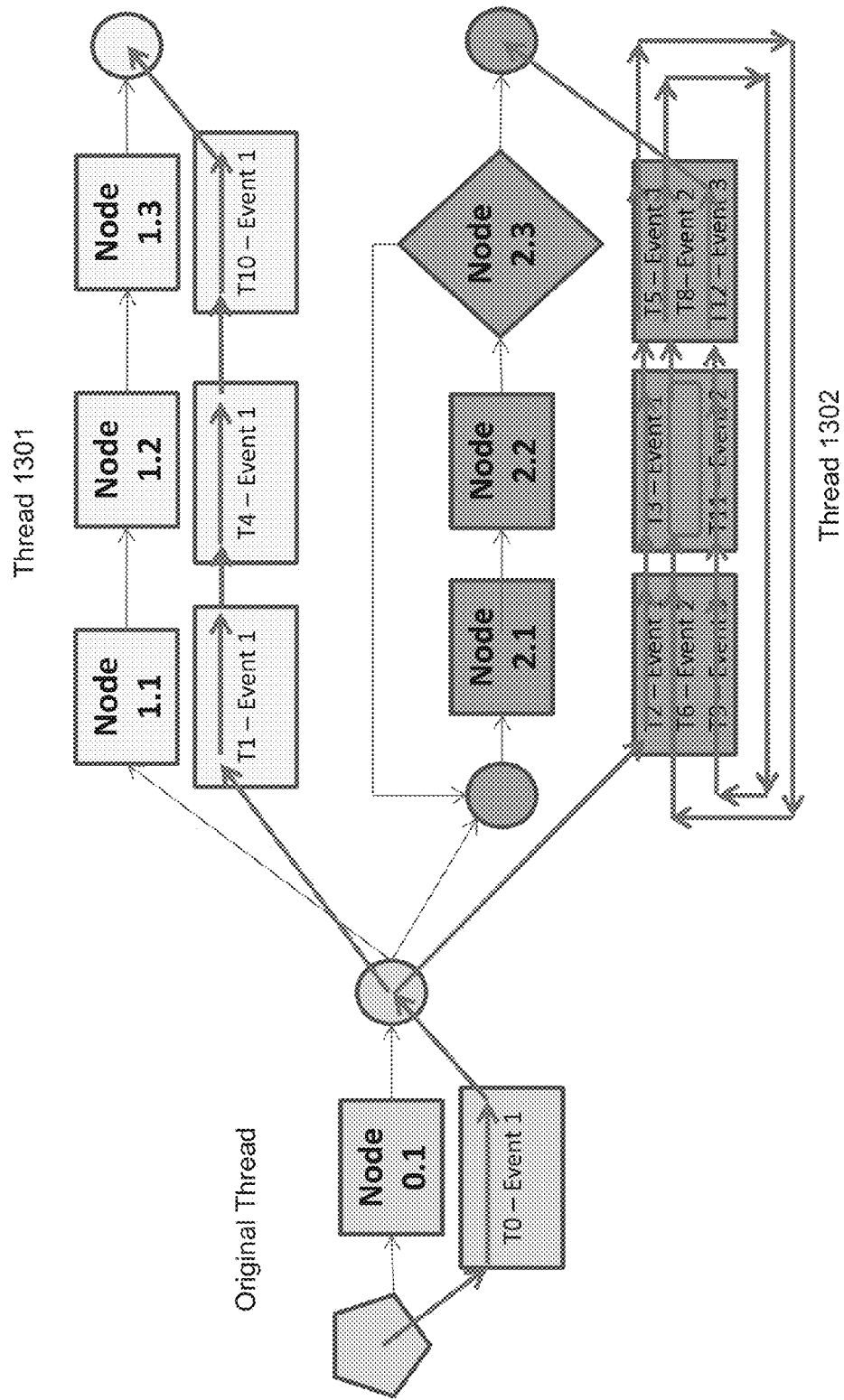
FIG. 13 illustrates an original thread splitting into parallel threads with one thread processing a looping sequence of events, according to an embodiment.

FIG. 13 shows a portion of a process map that includes an original thread that splits into two parallel threads 1301 and 1302 running concurrently. Query objects may be used to retrieve and assign events from the data storage 107 for each of the nodes 0.1, 1.1-1.3 and 2.1-2.3. For example, one event is retrieved for each of the nodes 0.1 and 1.1-1.3. Multiple events are retrieved for each of the nodes 2.1-2.3. Event times are determined for each of the events and the events are sorted for example by the mapping module 102 according to their event times within a node. T0-T12 represent the event times, whereby T0 is the earliest time and T12 is the latest time.

To determine the best fit of the retrieved events to the parallel threads 1301 and 1302 for the protocol, the protocol engine 103 finds the optimal time-dependent matches of the events to the nodes in the threads 1301 and 1302. The events are already assigned to the nodes prior to determining the best fit through the mapping performed by the mapping module 102. However, compliance with the protocol is determined by comparing the sequence of the events for the threads with the sequence of the nodes in the threads representing the expected actions to be performed at particular times within the workflow of the protocol. The protocol engine 103 determines the best fitting sequence so the comparison can be performed. FIG. 13 also shows that the matching process may loop through a thread so all events mapped to a node are accounted for. For example, multiple loops were performed for the nodes 2.1-2.3 to match all the events for the nodes.

To determine a best fitting sequence of events to the nodes, the recursive matching process may be performed based on event times and thread times. For example, the protocol engine 103 splits a core thread into multiple threads (e.g., threads 1301 and 1302) if encountering a fork and a thread time is maintained for each independent thread through the recursion. The thread time may be the event time of the previously matching event. The thread time is compared with event time to assigned events of each node to determine if an event is a match. If it is a match, the event is considered to be included in a particular slot in the sequence of events determined by the fitting process. With each recursive step, the thread whose time is the earliest is selected for advance. Also, when a match is detected, the thread time is updated to the matching event time and the matching process is performed for the next node in the earliest thread which is selected for advance. Determining the sequence of matching events is further illustrated with respect to FIGS. 14 and 15.

Figure 14:
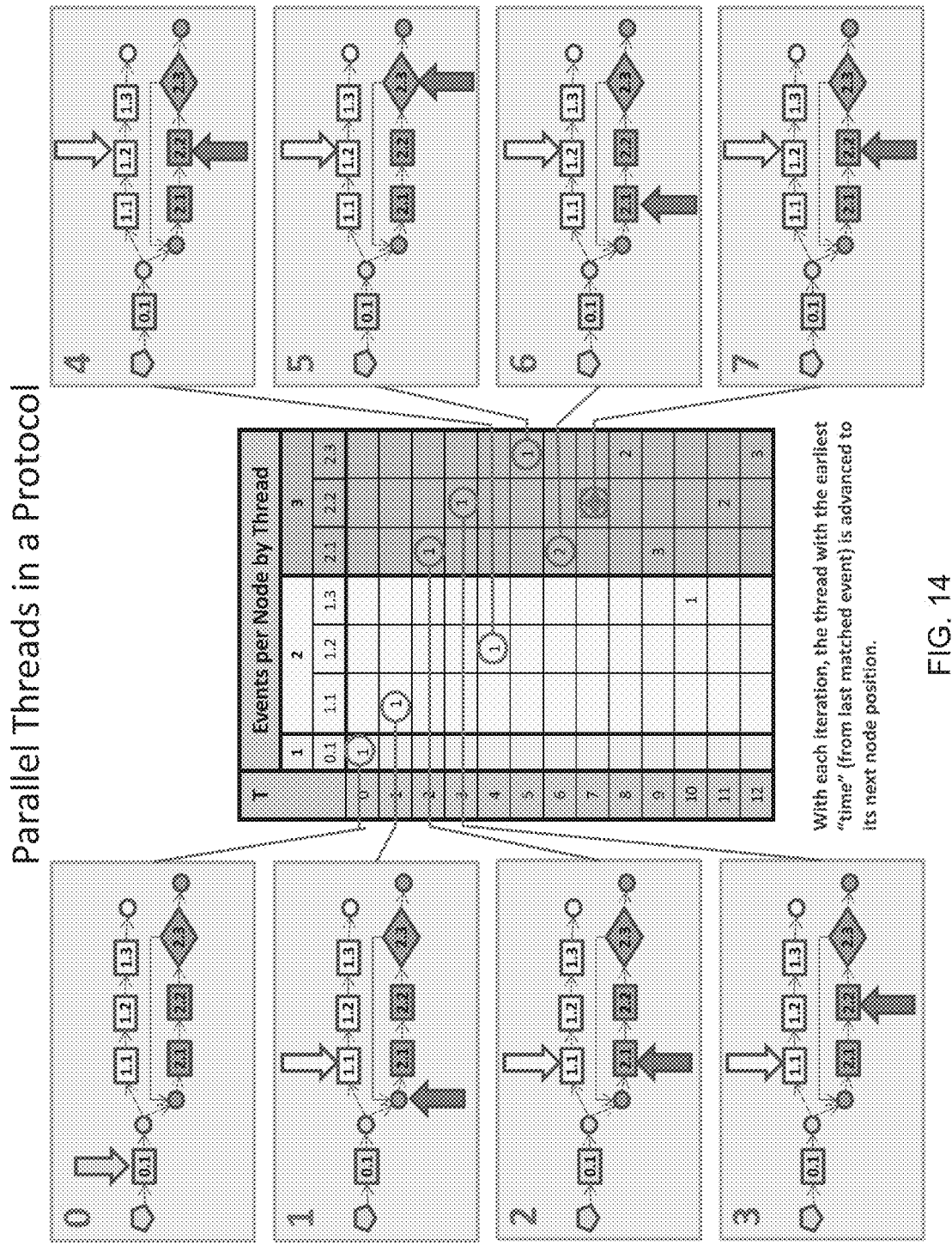
FIG. 14 illustrates a process of advancing through nodes in a best fit recursion per the time stamp on the sequence of events, according to an embodiment.

FIG. 14 shows the sequence for matching events for threads 1301 and 1302. The matching process starts with the earliest thread which is the original thread in this example and matches the event 1 to the node 0.1. The original thread is split into parallel threads 1301 and 1302 and the earliest thread is selected. Just after the fork, any of the parallel threads may be selected as the earliest thread because each of them adopts the thread time of the original thread, which is T0 for the matched event 1 of the node 0.1. In one example, the threads are ordered and the first thread in the order is selected. For example, thread 1301 is selected as the earliest thread and node 1.1 is matched with an event. The thread's time is used for comparison with a node's event to determine if it can be included in the sequence of matched events. There is only one event for the node. In this example, the event time for event 1 is after the thread time for thread 1301 so it is determined to be a matching event for node 1.1.

This is illustrated by step 1 in FIG. 14 which shows the event 1 for node 1.1 being a matched to node 1.1 and at this point the thread time of thread 1301 is set equal to the event time of event 1 which is T1. T0-T12 in the chart in FIG. 14 represent the event times of the matching events for the parallel threads 1301 and 1302. The protocol engine 113 has the option of assigning a missing event to the node if it provides a better match for the sequence.

With each iteration, the thread with the earliest time is advanced to its next node position. After event 1 at T1 is matched for the node 1.1, the thread pointer is at T1 which becomes the thread time. A next node from the parallel threads 1301 and 1302 may be selected with the earliest event after the thread time T1. In this example, it is event 1 for node 2.1 such as shown at step 2 in FIG. 14. The next earliest event after the thread time is at node 2.2, which is shown in step 3 in FIG. 14. This matching process continues as shown in steps 4-7 of FIG. 14. If the current node is a decision node, the next node is one of the outputs of the decision node. For example, node 2.3 is a decision node. The next node may be node 2.1 or the next node connected to the right of node 2.3. A missing event may be selected for a node. In this case, the thread time becomes the event time of the next earliest event. For example, if a missing event is matched at node 1.1, the thread time becomes T2 because it is the next earliest event in the parallel threads 1301 and 1302.

It should be noted that after step 5 in FIG. 14, the matching loops in the thread 1302 to match the multiple events for each node. For example, at steps 6-8, the matching is repeated for nodes 2.1-2.3. Also, at step 7, the protocol engine 103 determines that the best match for the node 2.2 is a missing event.

Figure 15:
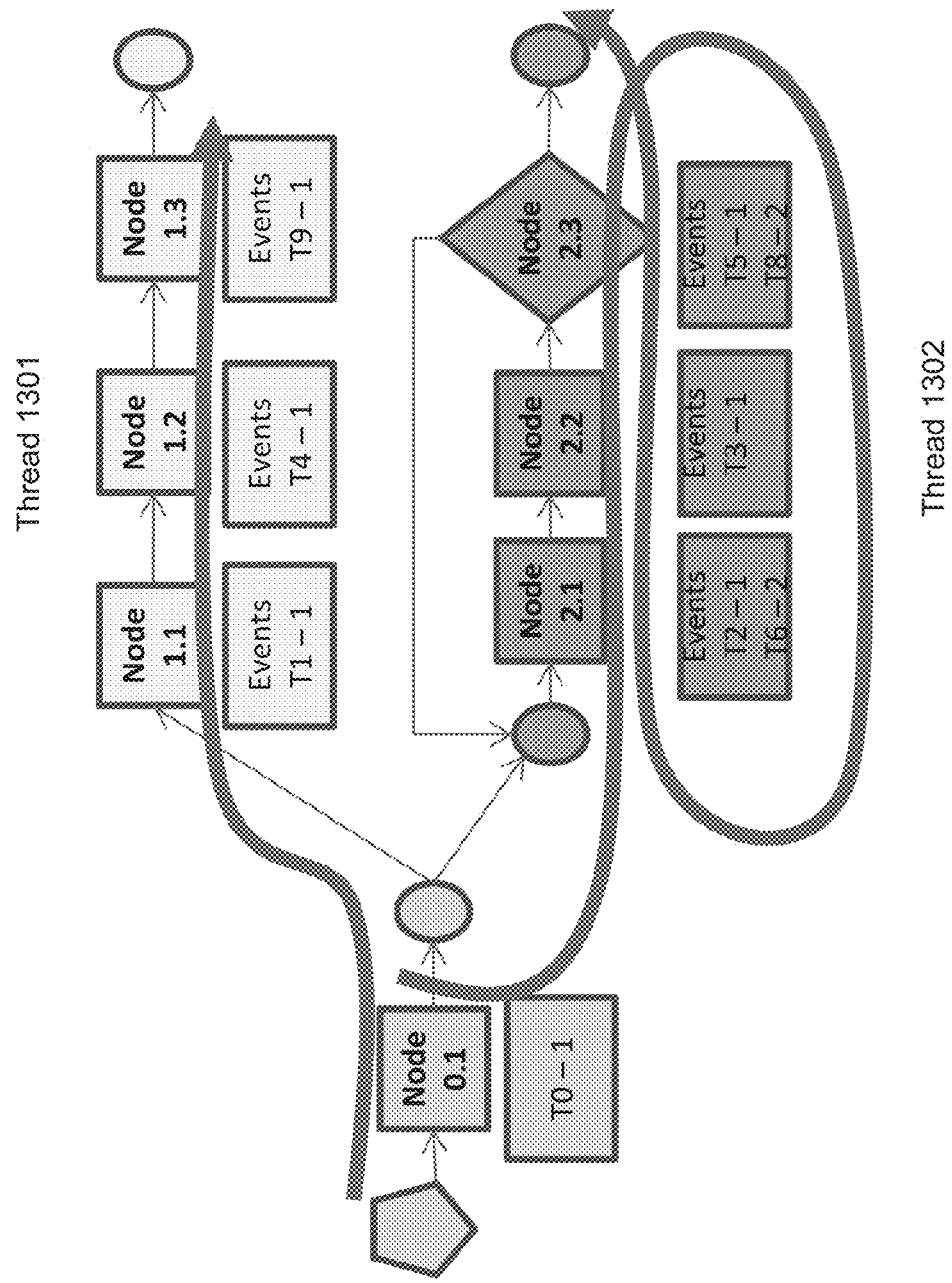
FIG. 15 illustrates threads and events assigned to nodes in the threads, according to an embodiment.
Figures 16A, 16B:
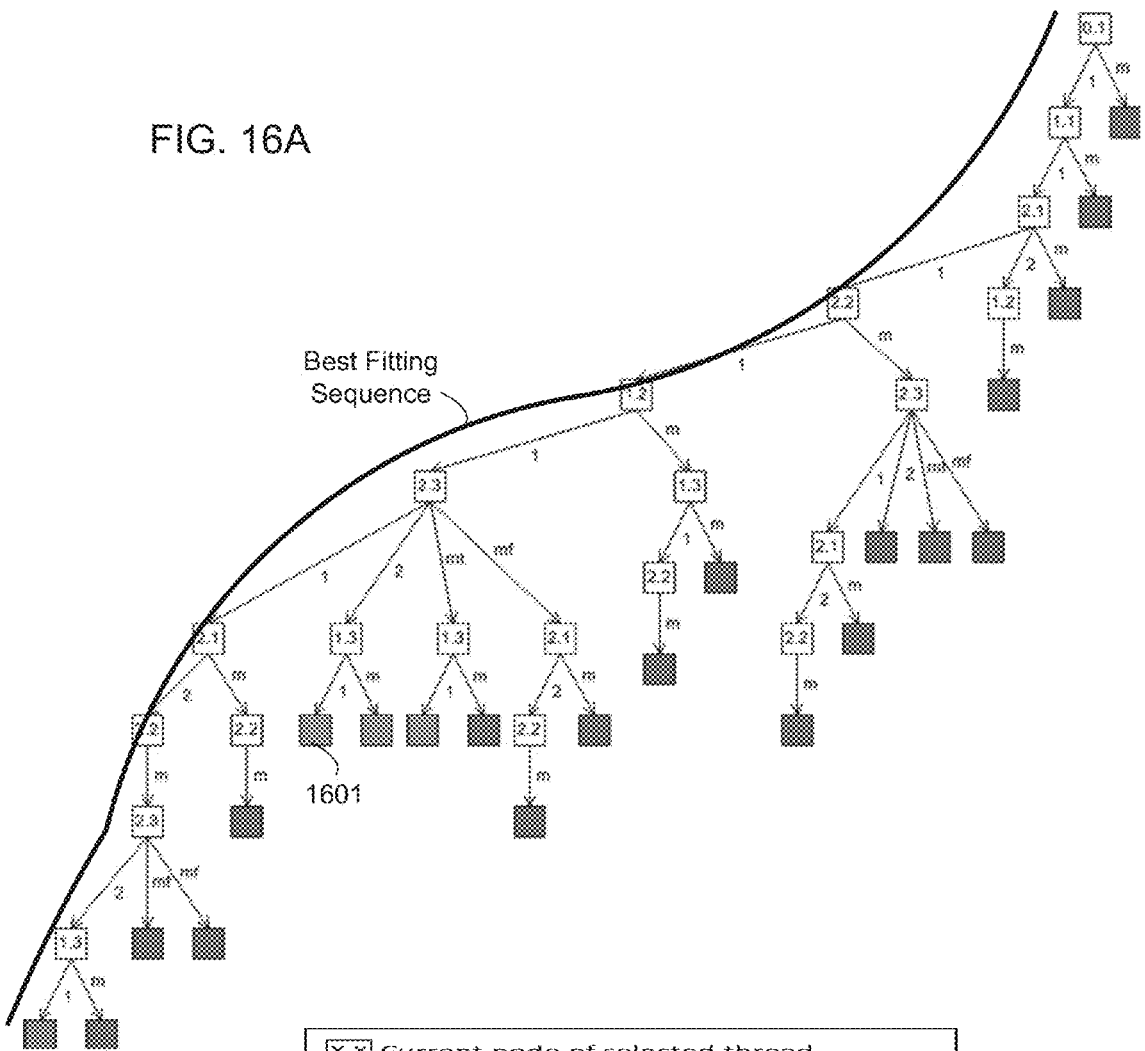
FIGS. 16A-B illustrate multiple event time-driven recursions determined through the recursive matching process for events in FIG. 15, according to an embodiment.

FIG. 15 shows threads 1301 and 1301 again but only shows one loop for thread 1302, so events for T9-T12 from FIGS. 13 and 14 are not shown. FIG. 16A shows the matching process for the events in FIG. 15 in the form of a graph to find a best fitting sequence. FIG. 16B shows the legend for the graph shown in FIG. 16A. The matching process shown in FIG. 16A is the same as shown in FIG. 14 for the events for T0-T8. FIG. 14 shows the best fitting sequence of events for the threads 1301 and 1302. FIG. 16A further illustrates how the best fitting sequence is determined through the recursive matching process. For example, at each node the protocol engine 113 tries to match each of the events having an event time greater than or equal to the thread time and a missing event to determine if it generates the best fitting sequence. FIG. 16A illustrates the matching of a missing event with "m". Also, each of the recursions shown in FIG. 16A start at the node 0.1 and end with a determination that the recursion is the best fitting sequence or with a determination that the recursion has completed and it is not the best possible sequence or with a determination that the recursion is not complete but the sequence being created by the current recursion path cannot mathematically be better than another recursion's sequence. A metric may be used to determine whether the recursion cannot mathematically be better than another recursion. In one example, the metric comprises a ratio of number of matched events over total number of times nodes are traversed for the recursion. In this example, the optimal value for this metric is 1 and the numerator cannot exceed the denominator. For example, for the best matching sequence shown in FIG. 16A, the denominator is 11 and the numerator is 10 because there is one missing event.

Node 0.1 has one event. The protocol engine 103 tries two different matches. The protocol engine 103 matches a missing event to the node 0.1 and also matches its event 1 to the node 0.1 as shown in FIG. 16A. The recursive matching stops for the missing event match because the protocol engine 103 determines that a better pattern is not possible for this recursion after matching node 0.1 with a missing event because the path from the 0.1 recursion attempts to match retrieved events first represented by the recursion path down the left side of the tree shown in FIG. 16A. However for the event 1 match, the recursive matching process continues to node 1.1. Node 1.1 has one event with an event time greater than its thread time, so protocol engine 103 matches a missing event to the node 0.1 and also matches its event 1. The recursion for the missing event match stops. However, the recursion for the event 1 match continues to node 2.1. Node 2.1 has 2 events that are possible matches. At node 2.1, the protocol engine matches event 1 for the node 2.1, and the recursion continues to node 2.2 because it has the next earliest event after the thread time, and so on as shown in FIG. 16A for the best fitting sequence. At node 2.1, the protocol engine 103 recurses for a match with event 2 and advances to the next node which is node 1.2 in this recursion. The next match for this recursion is a missing event and the recursion stops because the protocol engine 103 determines that the recursion cannot be better than the best fitting sequence shown on the left side. Also, at node 2.1, the protocol engine 103 matches a missing event, and the recursion stops because the protocol engine 103 determines that the recursion cannot be better than the best fitting sequence shown on the left side. This process continues advancing through the nodes in the parallel threads according to earliest thread times. At some points of the recursions, such as point 1601, the protocol engine 103 may determine that the recursion cannot mathematically be better than another recursion based on the metric and the recursion is stopped.

FIG. 17 shows pseudocode for the recursive matching process. The pseudocode indicates that the matching process is performed if it is mathematically possible to improve the matching. The thread with the earliest timestamp is selected. The node type of the current node is determined and different steps are performed depending on the type of node. If it is a start node, such as at the beginning of the process map, the thread is advanced to the next node. If the type is an activity or decision node, then a matching event is determined for the node as described above. The protocol engine 103 may use a maximum missing event threshold to prevent runaway recursion and determine whether to assign a missing event to a node. The protocol engine 103 does not assign a missing event to a node if the total number of missing events for the recursion would exceed the threshold.

If the node type is a rendezvous and continue node, a new thread is launched for each node connected to a link from the parent thread and the new threads are assigned the timestamp of the parent thread. A stop this thread node halts the matching process for the thread. A stop all thread except this thread node stops the matching process for all other threads and continues the process for the current thread. A protocol stop node stops the matching process and the protocol engine 103 determines the best fitting sequence.

Figure 18:
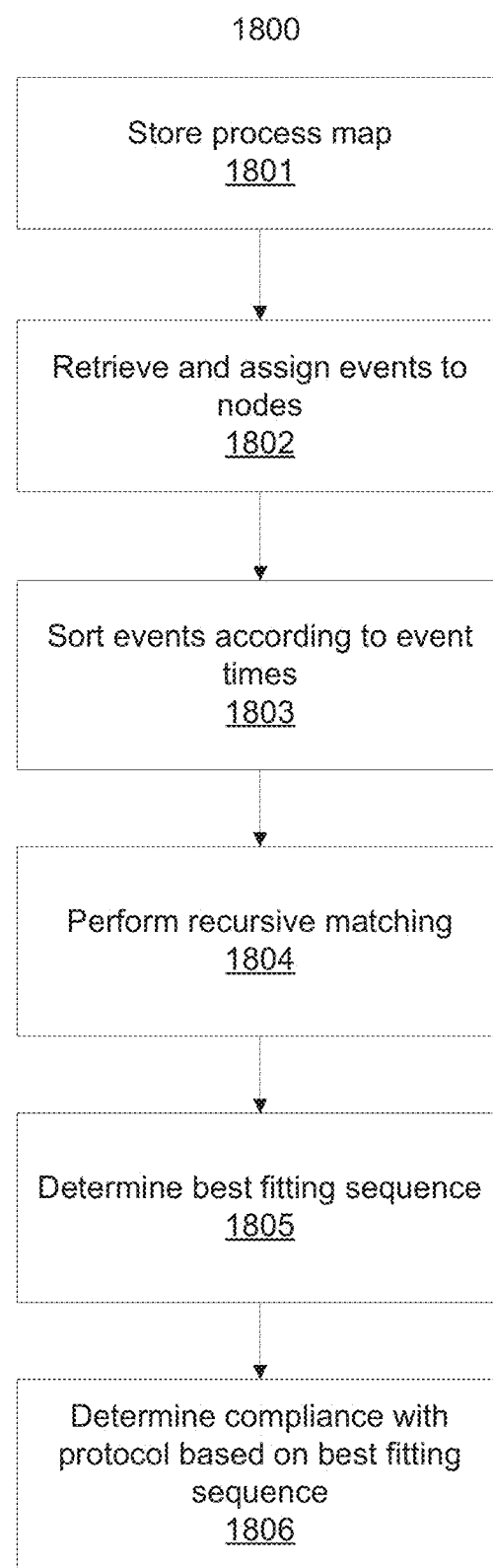
FIGS. 18-19 illustrate methods, according to embodiments.

The methods are described with respect to the system 100 shown in FIG. 1 by way of example. The methods may be performed by other systems. FIG. 18 shows a method 1800 according to an embodiment. At 1801 a process map is stored in the data storage 107 for a protocol. The process map may be created using the process map toolset 101. Query objects may be created for each node in the process map to retrieve events from the EMR data in the data storage 107 that is relevant to each node.

At 1802, the mapping module 102 retrieves and assigns events for nodes in the process map. The nodes may be decision and activity nodes in the process map. A query object assigned to each node may be called to retrieve the events for the node.

At 1803, the mapping module 102 sorts the events for each node by time. For example, the events assigned to each node are sorted from earliest to latest time.

At 1804, the protocol engine 103 performs the recursive matching process to determine matching sequences of events for the process map. The recursive matching process uses the event times of the events assigned to the nodes and the thread times to determine the matching sequences.

At 1805, the protocol engine 103 determines the best fitting sequence from the determined matching sequences. The best fitting sequence may be determined based on a metric. The metric may be calculated based on a number of times nodes are traversed, a number of matching events, and a number of missing events for the recursion or may be a ratio of number of matched events over total number of times nodes are traversed for a recursion.

At 1806, the compliance module 108 determines compliance with the protocol based on at least one metric for the best fitting sequence. The level of compliance may be measured based on the number of missing events. The reports may identify when the quality of care falls short and may be used to detect metrics associated with the causes, such as where, when, how and by whom. FIGS. 5 and 6 show other examples of compliance metrics used to measure and evaluate compliance with the protocol.

Figure 19:
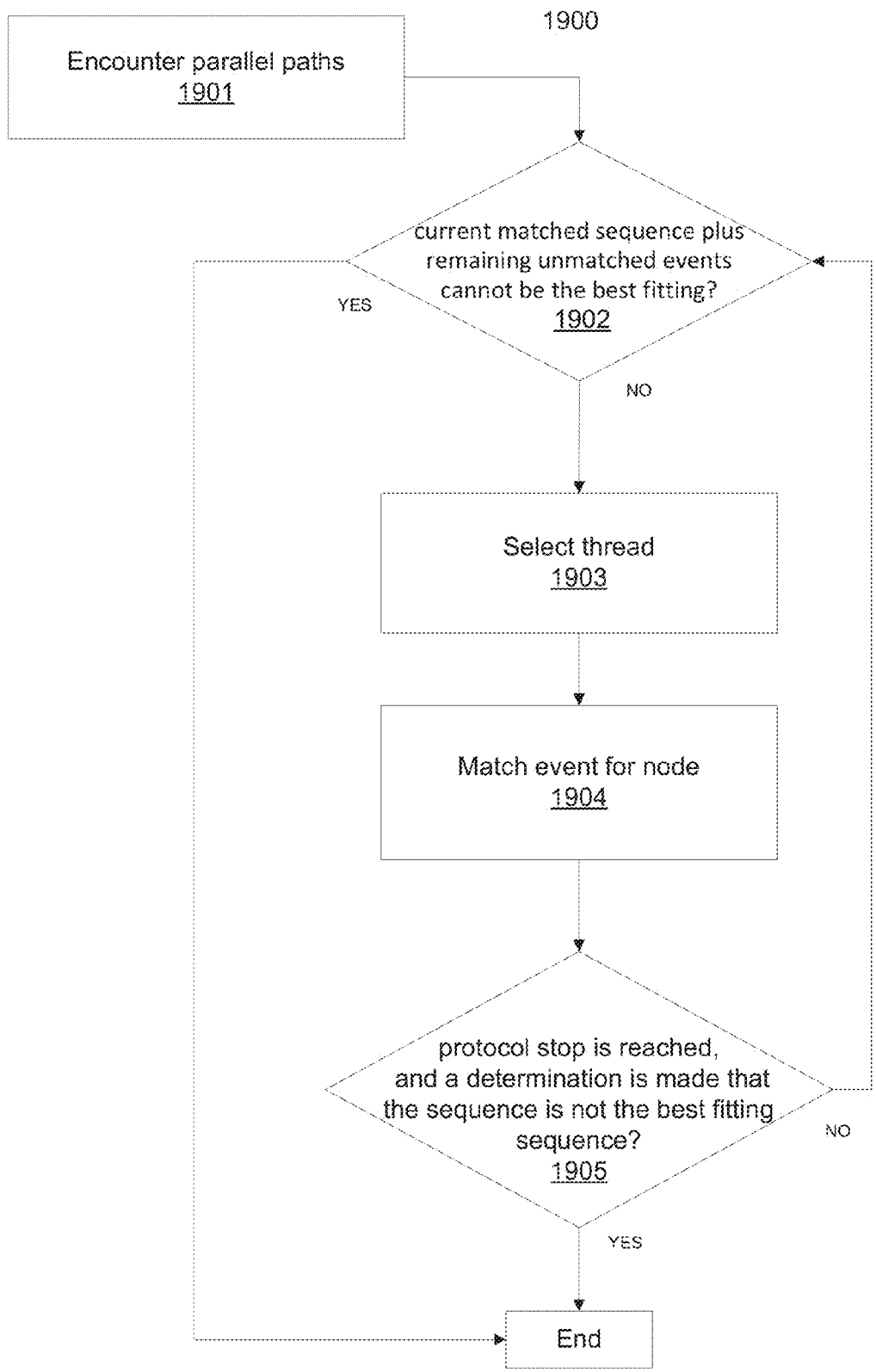

FIG. 19 illustrates a method for the recursive matching process and selecting the best fitting sequence of steps 1804 and 1805 of the method 1800. The recursive matching process for example starts at the start node of the process map and advances through the process map according to the thread time of each thread. A thread is a sequence nodes for example representing steps in a protocol ordered according to the sequence the steps are to be performed as specified by the protocol. A thread may split into multiple threads when it encounters a rendezvous and continue node with links to two or more nodes. A thread may end at a rendezvous and continue node, or a thread stop or protocol stop node. The thread time is determined from the event matched for the previous node before advancing to the next node in the protocol map.

At 1901, the protocol engine 103 encounters parallel paths in the process map. For example, referring to FIG. 13, the protocol engine 103, matches event 1 for node 0.1 and the thread is assigned the event time of event 1. The protocol engine 103 advances to the next node in the thread, where the thread splits into two parallel paths comprised of thread 1301 and thread 1302.

At 1902, the protocol engine 103 determines whether the current matched sequence plus remaining unmatched events cannot be the best fitting sequence. If yes, the process ends. If no, at 1903, the thread with the earliest time is selected. For example, thread 1301 is selected because node 1.1 has an earlier event time than the events for node 2.1. Each thread maintains its own thread time.

At 1904, the protocol engine 103 matches an event for the next node in the selected thread. The matching includes identifying time qualifying events assigned to the node. For example, a time-qualifying event is any event with an event time later than or equal to the thread time. One of the identified events is selected as a match or a missing event is selected as a match.

At 1905, the protocol engine 103 determines whether a protocol stop is reached, and whether the sequence is not the best fitting sequence. If not, the recursive matching process repeats steps 1902-1905. Otherwise the process ends. The recursive matching process increments exactly one thread's position and then recurses into the next steps of the matching process identifying matching events for the recursion. The matching process attempts to use each time-qualifying event in each node and recurses to the next step of the matching. Attempting to use each time-qualifying event in a node is illustrated by the loops shown for thread 1302 in FIG. 13.

As discussed above, a recursion may be stopped if the protocol engine 1301 determines the recursion cannot mathematically be better than another recursion. One or more metrics may be used to determine whether the recursion cannot mathematically be better than another recursion and for determining whether a recursion is a best fit.

Some or all of the method and operations and functions described above may be provided as machine readable instructions, such as a computer program, stored on a computer readable storage medium, which may be non-transitory such as hardware storage devices or other types of storage devices. For example, they may exist as program(s) comprised of program instructions in source code, object code, executable code or other formats. An example of a computer readable storage media includes a conventional computer system RAM, ROM, EPROM, EEPROM, and magnetic or optical disks or tapes.

Figure 20:
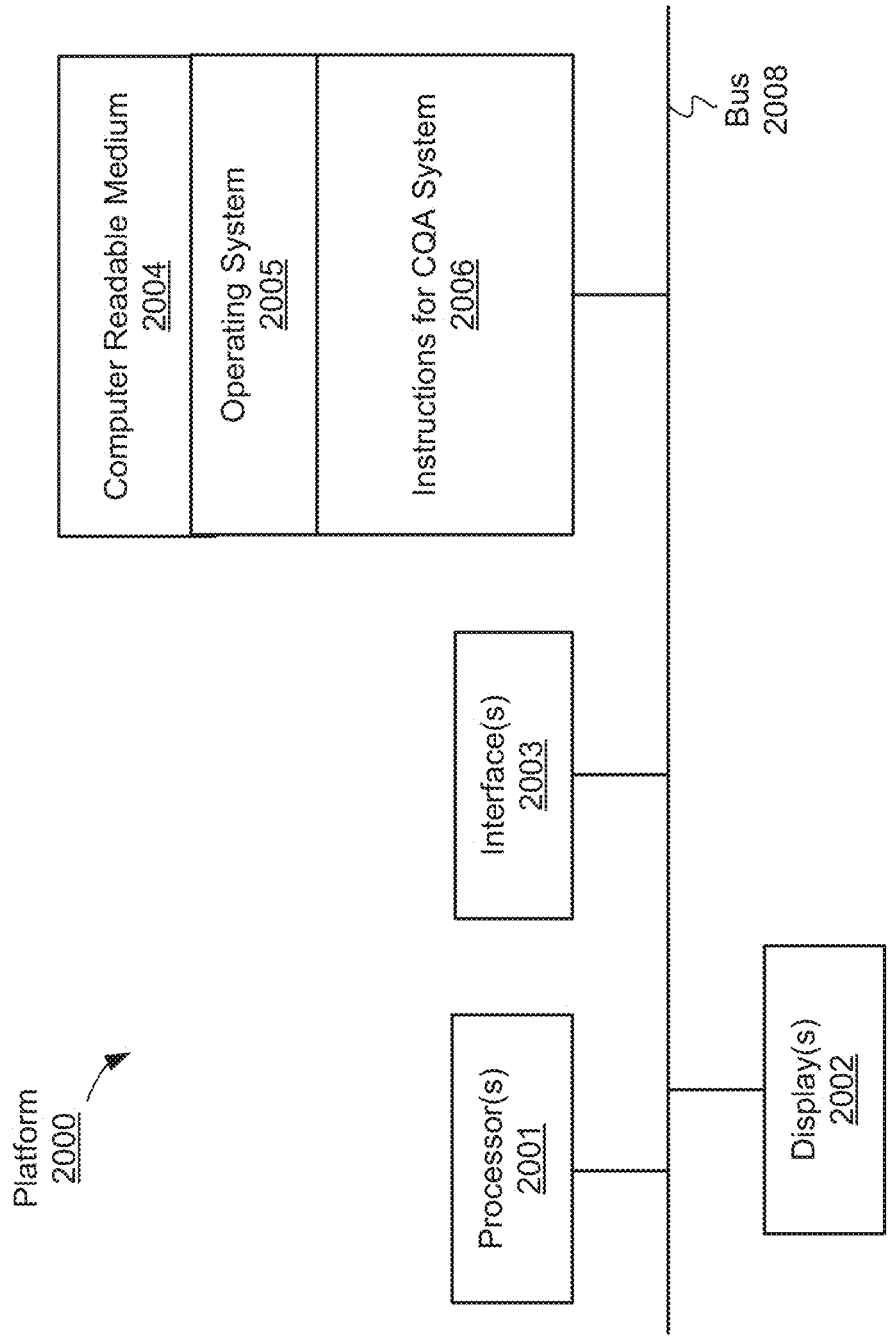
FIG. 20 illustrates a computer system that is operable to be used for the CQA system, according to an embodiment.

Referring to FIG. 20, there is shown a computer platform 2000 for the CQA system 100. It is understood that the illustration of the platform 2000 is a generalized illustration and that the platform 2000 may include additional components and that some of the components described may be removed and/or modified without departing from a scope of the platform 2000. Also, the CQA system 100 may be implemented in a distributed computing system, such as a cloud system.

The platform 2000 includes processor(s) 2001, such as a central processing unit, ASIC or other type of processing circuit; a display 2002, such as a monitor; an interface 2003, such as a network interface to a Local Area Network (LAN), a wireless 802.11x LAN, a 3G or 4G mobile WAN or a WiMax WAN; and a computer-readable medium 2004. Each of these components may be operatively coupled to a bus 2008. A computer readable medium (CRM), such as CRM 2004 may be any suitable medium which stores instructions for execution by the processor(s) 2001 for execution. For example, the CRM 2004 may be non-volatile media, such as a magnetic disk or solid-state non-volatile memory or volatile media. The CRM 2004 may also store other instructions or instruction sets, including word processors, browsers, email, instant messaging, media players, and telephony code.

The CRM 2004 may also store an operating system 2005, such as MAC OS, MS WINDOWS, UNIX, or LINUX and instructions 2006 for the CQA system 100. The operating system 2005 may be multi-user, multiprocessing, multitasking, multithreading, real-time and the like.

While the embodiments have been described with reference to the disclosure above, those skilled in the art are able to make various modifications to the described embodiments without departing from the scope of the embodiments as described in the following claims, and their equivalents.

What is claimed is:

1. A clinical quality analytics (CQA) system comprising:
a processor;
a non-transitory computer readable medium storing machine readable instructions executable by the processor; and
a data storage storing:
a process map determined from a protocol for medical treatment guidelines, the process map including a plurality of threads and each thread including nodes ordered in a chronological sequence,
query objects for the nodes in the plurality of threads, and
electronic medical record (EMR) data associated with a patient, the patient EMR data including events for medical treatment of the patient;
wherein the machine readable instructions comprise a process map toolset to generate the query objects for the nodes of the plurality of threads, wherein to generate the query objects the process map toolset, for each node:
identifies a concept identifier (ID) or a pointer to the concept ID associated with content of EMR data to be retrieved for the node;
determines query parameters constraining the EMR data to be retrieved for the node;
generates a structured query language statement including the concept ID and query parameters; and
stores the structured query language statement including the concept ID and query parameters in the data storage as the query object for the node;
wherein the machine readable instructions comprise a mapping module including an event retrieval module, wherein the event retrieval module, to retrieve events for each node:
identifies the stored query object for the node;
calls the identified query object to run the structured query language statement for the query object and retrieve events from the stored EMR data according to the structured query language statement; and
assign the retrieved events to the node in the process map, wherein each assigned event includes an event time; and
the mapping module is to sort the assigned events by their event times;
wherein the machine readable instructions comprise a protocol engine to determine a best fit of the events retrieved for the nodes to the plurality of threads based on the event time for each event and a thread time for each thread, wherein to determine the best fit the protocol engine:
recursively matches the events to the nodes in the threads based on the event times and the thread times, wherein the recursive matching allows for a missing event to be assigned to a node, wherein to recursively match the events to the nodes in the threads, the protocol engine:
selects a thread from the plurality of threads having an earliest thread time, wherein the thread time for each thread is determined from a current matching event;
selects a node from the selected thread that is a next node in the thread to be matched;
assigns, to the selected node, a missing event or an event of the node that has an event time equal to or greater than the thread time;

wherein upon assignment of the event, updates the thread time to the event time of the assigned event; and repeats the selecting, assigning and updating for each successive node, in succession, in the thread until a stop in the thread is identified from the process map;

determines at least one metric for each recursion measuring an accuracy of the events matching the nodes in the process map, and selects one of the recursions as the best fit based on the at least one metrics for the recursion measuring the accuracy of the events matching the nodes.

2. The system of claim 1, wherein the protocol engine assigning the missing event includes assigning the missing event if a total number of missing events for the recursion is less than a threshold.

3. The system of claim 1, wherein the at least one metric includes, for each recursion, a number of times nodes are traversed, a number of matching events, and a number of missing events for the recursion.

4. The system of claim 1, wherein the at least one metric comprises a ratio of number of matched events over total number of times nodes are traversed in the recursion.

5. The system of claim 1, wherein the protocol engine recursively matching the events to the nodes in the threads includes abandoning a recursion during the matching of the events if the recursion cannot produce a better fit of matching events than a previous recursion as determined based on at least one metric.

6. The system of claim 1, wherein the process map comprises a plurality of different types of nodes including a start node identifying a start of the protocol, an activity or decision node wherein at least one event is to take place for the activity or decision node, a rendezvous and continue node wherein a new thread is launched from the rendezvous and continue node, a stop thread node, a stop all threads except current thread node, and a protocol stop node identifying an end of the protocol.

7. The system of claim 1, comprising:
a compliance module to determine a level of compliance of the patient's treatment with the protocol based on the best fit of the events to the protocol map; and
a user interface to provide a visual indication of compliance for each node operable to have an associated event.

8. The system of claim 1, wherein the plurality of threads include a thread that forks, and a plurality of parallel threads spawned from the thread that forks.

9. The system of claim 1, wherein the recursive matching includes repeating matching events for nodes in a thread until all events for the nodes in the thread are matched or an end in the protocol is reached.

10. A method of determining a best fit of events for a process map representing a protocol, the method comprising:

storing a process map determined from a protocol, the process map including a plurality of threads and each thread including nodes ordered in a chronological sequence according to a workflow of the protocol;

storing query objects for the nodes in the plurality of threads, storing electronic medical record (EMR) data associated with a patient, the patient EMR data including events for medical treatment of the patient;

generating the query objects for the nodes of the plurality of threads, wherein generating the query objects the comprises:

identifying a concept identifier (ID) or a pointer to the concept ID associated with content of EMR data to be retrieved for the node;

determining query parameters constraining the EMR data to be retrieved for the node;

generating a structured query language statement including the concept ID and query parameters; and storing the structured query language statement including the concept ID and query parameters as the query object for the node;

retrieving stored events for each node, wherein retrieving stored events comprises:

identifying the stored query object for the node;

calling the identified query object to run the structured query language statement for the query object and retrieve events from the stored EMR data according to the structured query language statement; and assigning the retrieved events to the node in the process map, wherein each assigned event includes an event time;

determining, by a processor, a best fit of the events retrieved for the nodes to the plurality of threads based on the event time for each event assigned to the nodes and a thread time for each thread, wherein determining the best fit includes:

recursively matching the events to the nodes in the threads based on the event times and the thread times, wherein the recursive matching allows for a missing event to be assigned to a node, wherein recursively matching the events to the nodes in the threads comprises:

selecting a thread from the plurality of threads having an earliest thread time, wherein the thread time for each thread is determined from an event time for an event matched to a previous node;

selecting a node from the selected thread that is a next node in the thread to be matched;

assigning, to the selected node, a missing event or an event of the node that has an event time equal to or greater than the thread time;

wherein upon assignment of the event, updating the thread time to the event time of the assigned event; and repeating the selecting, assigning and updating for each successive node, in succession, in the thread until a stop in the thread is identified from the process map;

determining at least one metric for each recursion measuring an accuracy of the events matching the nodes in the process map; and selecting one of the recursions as the best fit based on the at least one metrics for the recursion measuring the accuracy of the events matching the nodes; and determining compliance with the protocol based on the best fit of the events.

11. The method of claim 10, wherein the at least one metric includes, for each recursion, a number of times nodes are traversed, a number of matching events, and a number of missing events for the recursion.

12. The method of claim 10, wherein the recursive matching includes abandoning a recursion during the matching of the events if the recursion cannot produce a better fit of matching events than a previous recursion as determined based on the at least one metric.

13. The method of claim 10, wherein the recursive matching includes repeating matching events for nodes in a thread until all events for the nodes in the thread are matched.

14. The method of claim 10, wherein the plurality of threads include a thread that forks, and a plurality of parallel threads spawned from the thread that forks.

15. A non-transitory computer readable medium including machine readable instructions executed by at least one processor to:
generate query objects including structured query language statements to retrieve stored data from a data storage according to a process map, wherein the process map includes a plurality of threads and each thread including nodes ordered in a chronological sequence, and
for each node of the plurality of threads, to generate the query objects, the at least one processor, executing the machine readable instructions, is to:
identify a concept identifier (ID) or a pointer to the concept ID associated with content of EMR data to be retrieved for the node;
determine query parameters constraining the EMR data to be retrieved for the node;
generate a structured query language statement including the concept ID and query parameters; and
store the structured query language statement including the concept ID and query parameters in the data storage as the query object for the node;
map events from the stored data to the nodes in the process map, wherein to map events, the at least one processor, executing the machine readable instructions is to, for each node:
identify the stored query object for the node;
call the identified query object to run the structured query language statement for the query object and retrieve events from the stored data according to the structured query language statement; and
assign the retrieved events to the node in the process map, wherein each assigned event includes an event time; and
determine a best fit of the events to the plurality of threads based on the event time for each event retrieved for the nodes and a thread time for each thread, wherein to determine best fit, the at least one processor, executing the machine readable instructions is to:
recursively match the events to the nodes in the threads based on the event times and the thread times, wherein the recursive matching allows for a missing event to be assigned to a node, wherein to recursively match the events to the nodes in the threads, the at least one processor, executing the machine readable instructions is to:
select a thread from the plurality of threads having an earliest thread time, wherein the thread time for each thread is determined from an event time for an event matched to a previous node;
select a node from the selected thread that is a next node in the thread to be matched;
assign, to the selected node, a missing event or an event of the node that has an event time equal to or greater than the thread time;
wherein upon assignment of the event, update the thread time to the event time of the assigned event; and
repeat the selecting, assigning and updating for each successive node, in succession, in the thread until a stop in the thread is identified from the process map;
determine at least one metric for each recursion measuring an accuracy of the events matching the nodes in the process map; and
select one of the recursions as the best fit based on the at least one metrics for the recursion measuring the accuracy of the events matching the nodes.

16. The non-transitory computer readable medium of claim 15, wherein the instructions are executed to determine a best fit of events for each of a plurality of individuals for which the protocol was applied and determine a correlation between missing events in the best fits and outcomes for the plurality of individuals resulting from applying the protocol to the plurality of individuals.

* * * * *

UNITED STATES PATENT AND TRADEMARK OFFICE
CERTIFICATE OF CORRECTION

PATENT NO. : 9,864,837 B2
APPLICATION NO. : 13/781397
DATED : January 9, 2018
INVENTOR(S) : Dennis Carroll et al.

It is certified that error appears in the above-identified patent and that said Letters Patent is hereby corrected as shown below:

In Column 15, Line 12, Claim 1, "metrics" should read "metric".
In Column 16, Line 55, Claim 10, "metrics" should read "metric".
In Column 18, Line 32, Claim 15, "metrics" should read "metric".

Signed and Sealed this
First Day of May, 2018

Andrei Iancu
*Director of the United States Patent and Trademark Office*